United States Patent
Burnouf et al.

(10) Patent No.: US 12,098,217 B2
(45) Date of Patent: Sep. 24, 2024

(54) FUSION PEPTIDES AS ANTIMICROBIAL AGENTS

(71) Applicants: CENTRE NATIONAL DE LA RECHERCHE SCIENTIFIQUE, Paris (FR); UNIVERSITÉ DE STRASBOURG, Strasbourg (FR); INSTITUT POLYTECHNIQUE DE BORDEAUX, Talence (FR); UNIVERSITÉ DE BORDEAUX, Bordeaux (FR)

(72) Inventors: Dominique Burnouf, Brumath (FR); Gilles Guichard, Gradignan (FR); Jerôme Wagner, Strasbourg (FR)

(73) Assignees: CENTRE NATIONAL DE LA RECHERCHE SCIENTIFIQUE, Paris (FR); UNIVERSITÉ DE STRASBOURG, Strasbourg (FR); INSTITUT POLYTECHNIQUE DE BORDEAUX, Talence (FR); UNIVERSITÉ DE BORDEAUX, Bordeaux (FR)

( * ) Notice: Subject to any disclaimer, the term of this patent is extended or adjusted under 35 U.S.C. 154(b) by 175 days.

(21) Appl. No.: 17/423,982

(22) PCT Filed: Jan. 17, 2020

(86) PCT No.: PCT/EP2020/051109
§ 371 (c)(1),
(2) Date: Jul. 19, 2021

(87) PCT Pub. No.: WO2020/148420
PCT Pub. Date: Jul. 23, 2020

(65) Prior Publication Data
US 2022/0002344 A1    Jan. 6, 2022

(30) Foreign Application Priority Data

Jan. 18, 2019 (EP) .................... 19305065

(51) Int. Cl.
C07K 7/08 (2006.01)
C07K 7/06 (2006.01)

(52) U.S. Cl.
CPC ............ C07K 7/06 (2013.01); C07K 7/08 (2013.01); C07K 2319/10 (2013.01)

(58) Field of Classification Search
None
See application file for complete search history.

(56) References Cited

U.S. PATENT DOCUMENTS

2014/0287989 A1    9/2014    Burnouf et al.

OTHER PUBLICATIONS

International Search Report dated Mar. 6, 2020 in International Application No. PCT/EP2020/051109.
European Search Report dated Jun. 12, 2019 in European Application No. 19 30 5065.
Knappe, D., et al, "Oncocin (VDKPPYLPRPRPPRRIYNR-NH2): A Novel Antibacterial Peptide Optimized against Gram-Negative Human Pathogens", Jul. 22, 2010, pp. 5240-5247, vol. 53, No. 14, J Med Chem.
Taniguchi, M., et al, "Pyrrhocoricin, a proline-rich antimicrobial peptide derived from insect, inhibits the translation process in the cell-free*Escherichia* coliprotein synthesis system", Oct. 23, 2015, pp. 591-598, vol. 121, No. 5, J Biosci. Bioeng.
Vitali, A., "Proline-Rich Peptides: Multifunctional Bioactive Molecules as New Potential Therapeutic Drugs", Jan. 1, 2015, pp. 147-162, vol. 16, Curr Protein Peptide Sci.
Wolff, et al., "Structure-Based Design of Short Peptide Ligands Binding onto the *E. coli* Processivity Ring", May 30, 2011, pp. 4627-4637, vol. 54, J. Med. Chem.
Dalrymple, et al., "A universal protein-protein interaction motif in the eubacterial DNA replication and repair systems", Sep. 25, 2001, pp. 11627-11632, vol. 98, No. 20, PNAS.

(Continued)

*Primary Examiner* — Thomas S Heard
(74) *Attorney, Agent, or Firm* — B. Aaron Schulman, Esq.; Stites & Harbison, PLLC

(57) ABSTRACT

The present invention relates to a fusion peptide having one of the following formulae: P1-L-P2 (I) or P2-L-P1 (II) wherein P1 is chosen from the proline-rich antimicrobial peptides; Lisa peptide linker; and P2 has the following formula (III): wherein m is 0 or 1; n is an integer comprised between 0 and 9; p is an integer comprised between 0 and 10; r is 0, 1 or 2; s is 0 or 1; Gln is glutamine; $R^1$ is the side chain of arginine or lysine; $R^2$ is for example a $-(CH_2)-C_{3-6}$-cycloalkyl group optionally substituted; $R^3$ is for example a $C_{1-8}$-alkyl group; $R^4$ is in particular a $C_{1-8}$-alkyl group optionally substituted by a $C_{3-6}$-cycloalkyl group; $R^5$ is for example a $-(CH_2)-C_{3-6}$-cycloalkyl group; $R^6$ is in particular $-COOH$, wherein, when the fusion peptide has the formula (II), its C-terminus contains a $-CO-$ group engaged in a peptide bond with said linker.

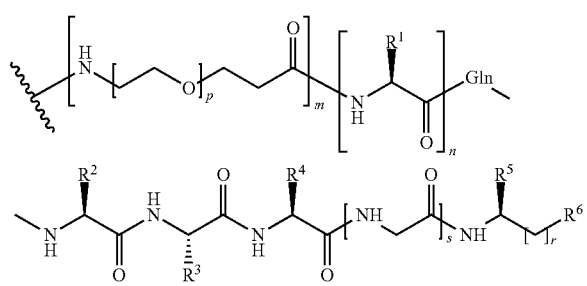

Figure 1:
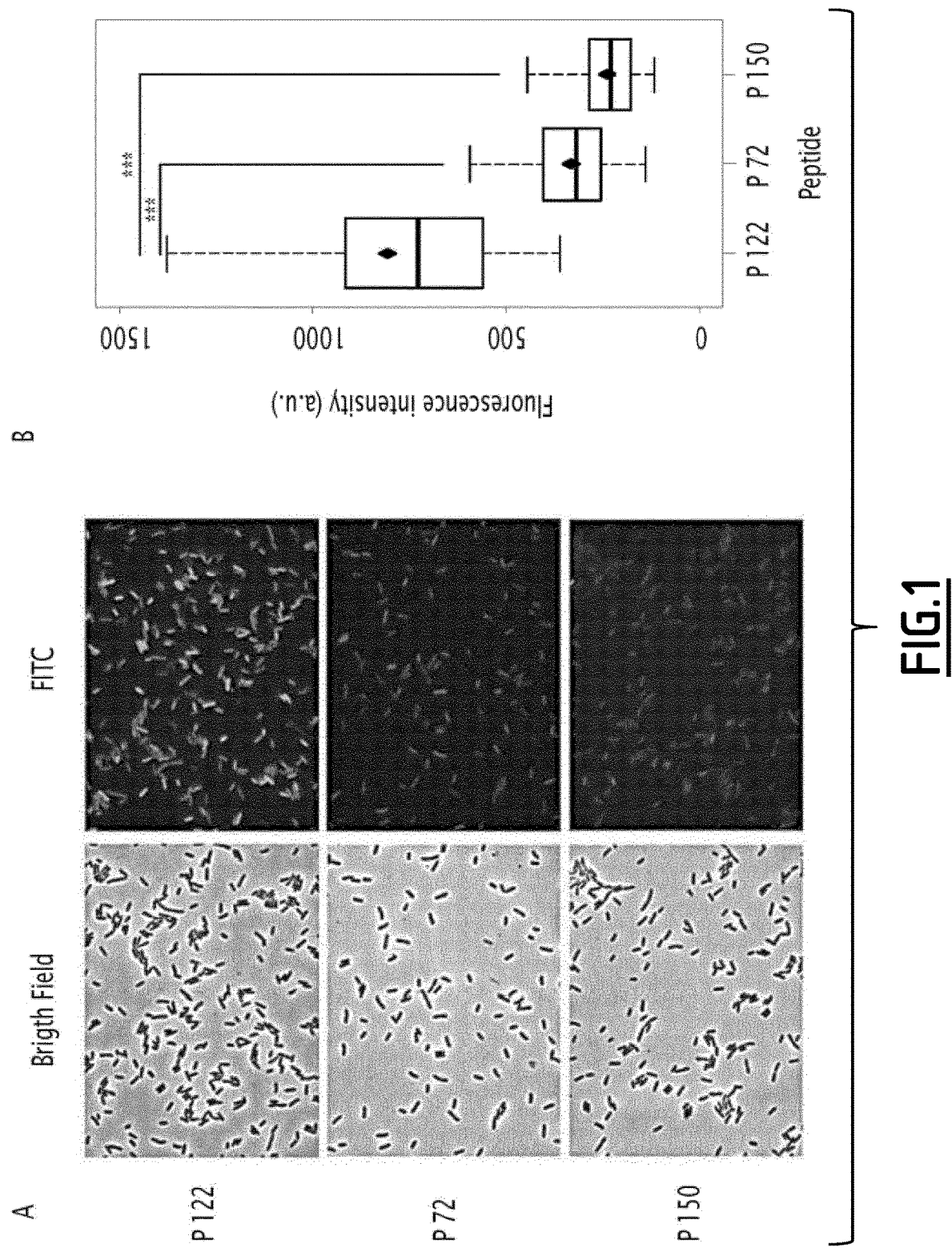

18 Claims, 4 Drawing Sheets
Specification includes a Sequence Listing.

(56) References Cited

OTHER PUBLICATIONS

Georgescu, et al. "Structure of small-molecule inhibitor of a DNA polymerase sliding clamp", Aug. 12, 2008, pp. 11116-11121, vol. 105, No. 32, PNAS.
Lopez de Saro, et al. "Interaction of the β sliding clamp with MutS, ligase, and DNA polymerase I" Jul. 17, 2001, pp. 8376-8380, vol. 98, No. 15, PNAS.
Wolff, et al., "Differential Modes of Peptide Binding onto Replicative Sliding Clamps from Various Bacterial Origins", Aug. 29, 2014, pp. 7565-7576, vol. 57, J. Med. Chem.
Krizsan, et al., "Insect-Derived Proline-Rich Antimicrobial Peptides Kill Bacteria by Inhibiting Bacterial Protein Translation at the 70 S Ribosome", 2014, pp. 12236-12239, Angew. Chem. Int.
Kong, et al., "Three-Dimensional Structure of the β Subunit of *E. coli* DNA Polymerase III Holoenzyme: A Sliding DNA Clamp", May 1, 1992, pp. 425-437, vol. 69, Cell.
Knappe, et al., "Oncocin (VDKPPYLPRPRPPRRIYNR-$NH_2$): A Novel Antibacterial Peptide Optimized against Gram-Negative Human Pathogens", 2010, pp. 5240-5247, vol. 53, J. Med. Chem.
Knappe, et al., "Rational Design of Oncocin Derivatives with Superior Protease Stabilities and Antibacterial Activities Based on the High-Resolution Structure of the Oncocin-Dnak Complex", 2011, pp. 874-876, No. 12, ChemBioChem.
Hoffmann, et al., "Range of activity and metabolic stability of synthetic antibacterial glycopeptides from insects", 1999, pp. 459-467, Biochimica et Biophysica Act 1426.
Taniguchi, et al., "Pyrrhocoricin, a proline-rich antimicrobial peptide derived from insect, inhibits the translation process in the cell-free *Escherichia coli* protein synthesis system", 2016, pp. 591-598, vol. 121, No. 5, Journal of Bioscience and Bioengineering.
Cociancich, et al., "Novel inducible antibacterial peptides from a hemipteran insect, the sap-sucking bug *Pyrrhocoris apterus*", 1994, pp. 567-575, vol. 300, Biochem J.

FUSION PEPTIDES AS ANTIMICROBIAL AGENTS

The present invention concerns new fusion peptides, in particular as antimicrobial agents, and also to therapeutic uses thereof. The present invention also relates to said fusion peptides for use for the treatment of bacterial infections.

Antimicrobial resistance has become an acute problem for public health and economy and threatens the progress of modern medicine. The World Health Organization has recently published a priority list of organisms (http://www.who.int/medicines/publications/global-priority-list-antibiotic-resistant-bacteria/en/) for which new antibiotic compounds must be developed to control their impact on human health. Other international, national and private agencies are setting up programs to foster research and development of such compounds. Within this frame, peptides that target the bacterial replication processivity factor, or sliding clamp (SC) have been previously designed (Wolff, P., Olieric, V., Briand, J. P., Chaloin, O., Dejaegere, A., Dumas, P., Ennifar, E., Guichard, G., Wagner, J., and Burnouf, D. Y. (2011). *Structure-based design of short peptide ligands binding onto the E. coli processivity ring*. J Med Chem 54, 4627-4637). This factor is a molecular hub which interacts with many proteins involved in bacterial DNA metabolism. In particular, all DNA polymerases interact with SC via a short peptide, for which a consensus sequence (QL[S/D]LF) has been defined (Dalrymple, B. P., Kongsuwan, K., Wijffels, G., Dixon, N. E., and Jennings, P. A. (2001). *A universal protein-protein interaction motif in the eubacterial DNA replication and repair systems*. Proc Natl Acad Sci USA 98, 11627-11632), and the hydrophobic pocket where these peptides interact has been acknowledged as a potential molecular target for new drug development (Georgescu, R. E., Yurieva, O., Kim, S. S., Kuriyan, J., Kong, X. P., and O'Donnell, M. (2008). *Structure of a small-molecule inhibitor of a DNA polymerase sliding clamp*. Proc Natl Acad Sci USA 105, 11116-11121; Lopez de Saro, F. J., and O'Donnell, M. (2001). *Interaction of the beta sliding clamp with MutS, ligase, and DNA polymerase I*. Proc Natl Acad Sci USA 98, 8376-8380). A structure-based strategy has been used to design small peptides that can interact more efficiently within the pocket of the *E. coli* clamp ($^{Ec}SC$) and define a minimal peptide which was used as a template sequence for further improvements of ligands and for studying the details of the ligand-target interaction (Wolff, P., Amal, I., Olieric, V., Chaloin, O., Gygli, G., Ennifar, E., Lorber, B., Guichard, G., Wagner, J., Dejaegere, A., and Burnouf, D. Y. (2014). *Differential modes of peptide binding onto replicative sliding clamps from various bacterial origins*. J Med Chem 57, 7565-7576). However, a strong limitation in the further development of these peptides into antimicrobial agents is their inability to cross the bacterial cell membrane.

The aim of the present invention is thus to provide an efficient antimicrobial compound, and being able to cross the bacterial cell membrane.

Therefore, the present invention relates to a fusion peptide having one of the following formulae:

$$P1-L-P2 \quad (I)$$

or $$P2-L-P1 \quad (II)$$

wherein:
P1 is chosen from the proline-rich antimicrobial peptides;
L is a peptide linker; and
P2 has the following formula (III):

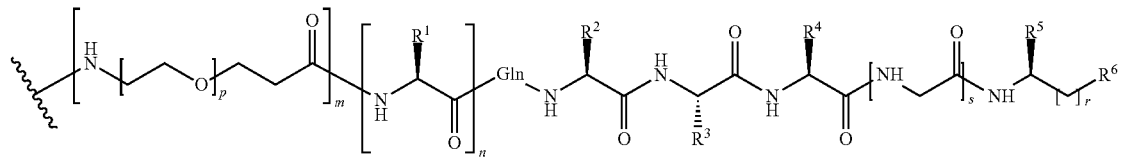

wherein:
m is 0 or 1;
n is an integer comprised between 0 and 9;
p is an integer comprised between 0 and 10;
r is 0, 1 or 2;
s is 0 or 1;
Gln is glutamine;
$R^1$ is the side chain of arginine or lysine;
$R^2$ is a —$(CH_2)$—$C_{3-6}$-cycloalkyl group optionally substituted by a halogen and/or by a group selected amongst —$NH_2$, —NH—CO—$R^a$, —$CO_2H$, —$NHR^a$ and —$NR^aR^b$, wherein $R^a$ and $R^b$ are independently a $C_{1-4}$-alkyl group;
$R^3$ is selected in the group consisting of a $C_{1-8}$-alkyl group, the side chain of arginine or lysine, —$(CH_2)_q$—$CO_2R^{7a}$, —$(CH_2)_q$—CO—$NHR^{7b}$, —$CH_2OR^8$ and —$(CH_2)_qNHR^8$, wherein
q is 1, 2, 3 or 4,
$R^{7a}$ is a hydrogen atom, a $C_{1-8}$-alkyl group, a $C_{4-12}$-alkylene group forming together with $R^6$ a lactone or a polyether ring, or a $C_{4-12}$-alkenylene, forming together with $R^6$ a lactone or a polyether ring,
$R^{7b}$ is a hydrogen atom, a $C_{1-8}$-alkyl group, or —$(CH_2)_{q'}$—NH— with q' being an integer between 2 and 8 inclusive and forming together with $R^6$ a lactam,
$R^8$ is a hydrogen atom, a $C_{1-8}$-alkyl group, a $C_{4-12}$-alkylene group forming together with $R^6$ a lactone or a polyether ring, or a $C_{4-12}$-alkenylene, forming together with $R^6$ a lactone or a polyether ring,
$R^9$ is a hydrogen atom, or $R^9$ together with $R^6$ form a lactam;
$R^4$ is a $C_{1-8}$-alkyl group optionally substituted by a $C_{3-6}$-cycloalkyl group, or a halogen-$C_{1-4}$-alkyl group;
$R^5$ is selected in the group consisting of a —$(CH_2)$—$C_{3-6}$-cycloalkyl group; —$(CH_2—CH_2)$—$C_{3-6}$-cycloalkyl group; a —$(CH_2)$—$C_{6-10}$-aryl group optionally substituted by a halogen, a $C_{1-12}$ alkyl group and/or a $C_{1-12}$ alkoxy group; a —$(CH_2—CH_2)$—$C_{6-10}$-aryl group optionally substituted by a halogen, a $C_{1-2}$ alkyl group and/or a $C_{1-2}$ alkoxy group; a —$(CH_2)$—$C_{5-10}$-heteroaryl group optionally substituted by a halogen and/or a $C_{1-2}$ alkyl group;
$R^6$ is —COOH, —$COOR^{10}$, —CO—$NH_2$, —CO—$NHR^{10}$, —$OR^{10}$ when r is 1 or 2, —NH—CO—

NHR$^{10}$ when r is 1 or 2, or R$^6$ is —CO—, —CO—O— or —O— and forms a lactam, a lactone, or a polyether ring with R$^{7a}$, R$^{7b}$, R$^8$ or R$^9$; wherein R$^{10}$ is a C$_{1-8}$-alkyl group optionally substituted by a C$_{6-10}$-aryl group; a C$_{3-6}$-cycloalkyl group; a C$_{6-10}$-aryl group optionally substituted by a halogen, a C$_{1-2}$-alkyl group and/or a C$_{1-2}$-alkoxy group, wherein, when the fusion peptide has the formula (II), its C-terminus contains a —CO— group engaged in a peptide bond with said linker L.

The fusion peptide of formula (I) of the invention is P1-L-P2, which means that the N-terminus of this fusion peptide is the N-terminus of P1 and the C-terminus of this fusion peptide is the C-terminus of P2.

The fusion peptide of formula (II) of the invention is P2-L-P1, which means that the N-terminus of this fusion peptide is the N-terminus of P2 and the C-terminus of this fusion peptide is the C-terminus of P1.

The fusion peptide of the invention may also be referred as N-ter[P1-L-P2] (I) or N-ter[P2-L-P1] (II), respectively.

According to the invention, P1, L, and P2 are linked together by peptide bonds.

Preferably, the fusion peptide of the invention has the formula (I).

According to the invention, P1 is an antimicrobial peptide, which is chosen from the proline-rich antimicrobial peptides.

According to the invention, in formula (I), the N-terminus of P1 is free and its C-terminus is linked with L.

The present invention involves the use of a specific class of antimicrobial peptides, referred to as Proline rich Anti-Microbial Peptides (PrAMPs), as delivery vectors. These natural peptides are found in invertebrates and vertebrates and are part of the innate immune response. They are considered as a promising novel class of antibiotics and the cellular target that accounts for their biological activity, namely the peptide exit channel (PEC) of the bacterial ribosome, has been recently identified (Krizsan, A., Volke, D., Weinert, S., Strater, N., Knappe, D., and Hoffmann, R. (2014). *Insect-derived proline-rich antimicrobial peptides kill bacteria by inhibiting bacterial protein translation at the 70S ribosome. Angew Chem Int Ed Engl* 53, 12236-12239).

Preferably, P1 is a peptide comprising from 13 to 40 amino acid residues and contains at least one central segment consisting of the sequence SEQ ID NO:1:

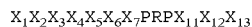

wherein: X$_1$ is V, R or P; X$_2$ is D, R, P or F; X$_3$ is K, P, V or R; X$_4$ is P, G, R, Y, Q or A; X$_5$ is S, G, D, P, I, O or Q; X$_6$ is Y, P, V, I or R; X$_7$ is L, P, Q or R; X$_{11}$ is P, R, T or G; X$_{12}$ is P, W, H or R; and X$_{13}$ is P, Hyp or R, O being ornithine and Hyp being hydroxyl-proline.

According to an embodiment, P1 contains at the N-terminus of its central segment from 0 to 10 amino acid residues. According to an embodiment, P1 contains at the C-terminus of the central segment from 0 to 18 amino acid residues. Preferably, these amino acid residues are selected from the group consisting of natural L-amino acids, D-amino acids, modified amino acids, non-natural amino acids, and mixtures thereof.

As used herein, the term "amino acid" is understood to include: the 20 naturally occurring amino acids i.e. alanine, arginine, asparagine, aspartic acid, cysteine, glutamic acid, glutamine, glycine, histidine, isoleucine, leucine, lysine, methionine, phenylalanine, praline, serine, threonine, tryptophan, tyrosine, and valine; amino acids harbouring the post-translational modifications which can be found in vivo such as hydroxyproline, L-tert-leucine, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

D-enantiomers of amino acids (also called D-amino acids) are referred to by the same letter as their corresponding L-enantiomer (also called L-amino acid), but in lower case. Thus, for example, the L-enantiomer of arginine is referred to as 'R', while the D-enantiomer is referred to as 'r'.

According to the invention, the following chemical modifications may be mentioned:
  modifications to the N-terminal and/or C-terminal ends of the peptides such as e.g. N-terminal acylation (preferably acetylation) or deamination, or modification of the C-terminal carboxyl group into an amide or an alcohol group;
  retro-inversions in which one or more naturally-occurring amino acids (L-enantiomer) are replaced with the corresponding D-enantiomers, together with an inversion of the amino acid chain (from the C-terminal end to the N-terminal end);
  azapeptides, in which one or more alpha carbons are replaced with nitrogen atoms; and/or
  betapeptides, in which the amino group of one or more amino acid is bonded to the β carbon rather than the α carbon.

The peptide includes amino acids modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini, it will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching.

As examples of modified amino acids, one may cite the amino acids resulting from post-translational modifications such as hydroxyproline (Hyp).

As examples of non-natural amino acids, one may cite ter-leucine (Tle).

According to an embodiment, the N-terminus of P1 further contains at least one, and preferably several, positively charged residue(s), such as arginine and lysine. According to an embodiment, the N-terminus of P1 further contains from 2 to 5, preferably 2 or 3, positively charged residue(s), and preferably 2 to 5, more preferably 2 or 3, arginine residues.

According to such embodiment, the peptides P1 are for example as follows: RRIRPRPPRLPRPRPRPLPFPRPGP (SEQ ID NO: 19) (bt-bactenecin-7), RRIRPRRPRLPRPR-PRPRPRPRSLP (SEQ ID NO: 20) (ch-bactenecin-7), RRLRPRRPRLPRPRPRPRPRPRSLP (SEQ ID NO: 21) (oa-bactenecin-7), RRRPRPPYLPRPRPPPFFPPRLPPR (SEQ ID NO: 22) (PR-39), RFRPPIRRPPIRPPFYPPFRP-PIRP (SEQ ID NO: 23) (bt-bactenecin-5), RFRPPIRRP-PIRPPFNPPFRPPVRP (SEQ ID NO: 24) (ch-bactenecin-5), OR RFRPPIRRPPIRPPFRPPFRPPVRP (SEQ ID NO: 25) (oa-bactenecin-5).

According to an embodiment, the N-terminus of P1 may be further modified for example by a N,N,N',N'-tetramethylguanidino group (gu).

As peptide P1, the followings may be mentioned here: GNNRPVYIPQPRPPHPRL (SEQ ID NO: 4) (Apidaecin-1 b), gu-ONNRPVYIPRPRPPHPRL-OH (SEQ ID NO: 5) (Api137), guONNRPVYIPQPRPPHPRL-NH2 (SEQ ID NO: 6) (Api88), guOWOWOWOWORPVYIPQPRPPHPRL (SEQ ID NO: 7) (Api794), YVPLPNVPQPGRRPFPTFPGQGPFNPKIKWPQ (SEQ ID NO: 8) (Abaecin), GKPRPYSPRPTSHPRPIRV (SEQ ID NO: 9) (Drosocin), GKPRPQQVPPRPPHPRL (SEQ ID NO: 10) (Ho+), GKPNRPRPAPIQPRPPHPRL (SEQ ID NO: 11) (Cd1+), SRWPSPGRPRPFPGRPKPIFRPRPC (SEQ ID NO: 12) (Arasin 1), VDKPPYLPRPXPPR-RIYNNR (SEQ ID NO: 13) (Oncocin), VDKPPYLPRPRP-PRrIYNr-NH$_2$ (SEQ ID NO: 2) (Onc112), VDKPPYLPR-PRPPPRrOYNO-NH$_2$ (O=ornithine) (SEQ ID NO: 14) (Onc72), VDKPPYLPRPRPHypRHypTleYNO-NH$_2$ (SEQ ID NO: 15) (Onc06), VDKPPYLPRPRWPRRIYNR-NH2 (SEQ ID NO: 16) (Onc15), VDKPDYRPRPRPPNM (SEQ ID NO: 17) (Metalnikowin-1), VDKGSYLPRPTP-PRPIYNRN (SEQ ID NO: 3) (Pyrrhocoricin), VDKGGYL-PRPTPPRPVYRS (SEQ ID NO: 18) (Riptocin), RRIRPRP-PRLPRPRPRPLPFPRPGP (SEQ ID NO: 19) (bt-bactenecin-7), RRIRPRRPRLPRPRPRPRPRSLP (SEQ ID NO: 20) (ch-bactenecin-7), RRLRPRRPRLPRPRPRPR-PRPRSLP (SEQ ID NO: 21) (oa-bactenecin-7), RRRPRP-PYLPRPRPPPFFPPRLPPR (SEQ ID NO: 22) (PR-39), RFRPPIRRPPIRPPFYPPFRPPIRP (SEQ ID NO: 23) (bt-bactenecin-5), RFRPPIRRPPIRPPFNPPFRPPVRP (SEQ ID NO: 24) (ch-bactenecin-5), RFRPPIRRPPIRPPFRPP-FRPPVRP (SEQ ID NO: 25) (oa-bactenecin-5), RRIRPRP-PRLPRPRPRPLPFPRPGPRPIPRPLPFP (SEQ ID NO: 26) (Bac7(1-35)), and RRIRFRPPYLPRPGRR-PRFPPPFPIPRIPRIP (SEQ ID NO: 27) (Tur1A).

Preferably, P1 is chosen from the following peptides: VDKPPYLPRPRPPRrIYNr-NH$_2$ (SEQ ID NO: 2), and VDKGSYLPRPTPPRPIYNRN (SEQ ID NO: 3), r representing D-arginine.

According to the invention, the peptide P1 is linked at its C-terminus with a peptide linker L.

Preferably, L comprises from 1 to 10 amino acids, preferably from 2 or 3 amino acids.

According to an embodiment, L contains any natural amino acid, preferably selected from the group consisting of: A, G, P, S, D, and E.

Preferably, L is chosen from the following amino acids or peptides: Gly-Pro, Gly-Gly, Pro-Gly, β-Ala-β-Ala, Sar-Sar, Gly-Glycolic acid, γ-Abu, 6-aminohexanoic acid, aminovaleric acid, and Gly-Gly-Gly, Sar representing sarcosine, and Abu representing aminobutyric acid.

As mentioned above, P2 has the formula (III).

In the above formula (III), the peptide linkages (—CO—NH—) can be replaced or modified to obtain synthetic pseudopeptides or peptidomimetics in which the peptide bond is modified, especially to become more resistant to proteolysis, provided the immunogenicity of and the toxicity of the molecule is not increased by this modification, and providing the pseudopeptide retains its affinity for the β interacting pocket.

The following definitions are set forth to illustrate and define the meaning and scope of the various terms used to describe the invention herein. The term "$C_{1-12}$-alkyl" refers to a branched or straight-chain monovalent saturated aliphatic hydrocarbon group of 1 to 12 (inclusive) carbon atoms. Similarly, the terms: "$C_{1-8}$-alkyl", "$C_{1-5}$-alkyl", "$C_{1-4}$-alkyl", "$C_{1-2}$-alkyl" and the like refer to branched or straight-chain monovalent saturated aliphatic hydrocarbon groups of, respectively, 1 to 8 (inclusive), 1 to 5 (inclusive), 1 to 4 (inclusive), 1 to 2 carbon atoms. This term is further exemplified by groups as methyl, ethyl, propyl, butyl, pentyl, hexyl, heptyl, octyl, nonyl, decyl, undecyl, dodecanyl and their branched isomers. The "alkyl" group can optionally be mono-, di-, tri- or multiply-substituted by a halogen and/or a $C_{6-10}$ aryl group, as defined below.

The term "$C_{1-8}$-alkyl-(O—CH$_2$—CH$_2$)$_t$—" refers to a —(O—CH$_2$—CH$_2$)$_t$— substituted $C_{1-8}$-alkyl group wherein the alkyl group is as defined above and t is an integer from 0 to 20 (inclusive), preferably 0, 1, 2, 3, 4, 5, 6, 7, 8, 9 or 10. Preferred —(O—CH$_2$—CH$_2$)$_t$-substituted alkyl group is a $C_{1-6}$-alkyl-(O—CH$_2$—CH$_2$)$_t$— group with t and alkyl as defined above.

The term "$C_{2-12}$-alkenyl" refers to a branched or straight-chain monovalent unsaturated aliphatic hydrocarbon group having one or more carbon double bonds, of 2 to 12 (inclusive) carbon atoms, preferably 2 to 8 (inclusive) carbon atoms, more preferably 2 to 4 (inclusive) carbon atoms. This term is further exemplified by groups as vinyl, propylenyl, butenyl, pentenyl, hexenyl, heptenyl, octenyl, nonenyl, decenyl, undecenyl, dodecenyl and their straight-chain and branched and stereo isomers. The "alkenyl" group can optionally be mono-, di-, tri- or multiply-substituted by a halogen and/or a $C_{6-10}$-aryl group, as defined below.

The term "$C_{1-12}$-alkylene" refers to a divalent $C_{1-12}$-alkyle with alkyl as defined above. Similarly, terms such as "$C_{4-12}$-alkylene" or "$C_{4-8}$-alkylene" and the like, refer to divalent $C_{4-12}$-alkyl or divalent $C_{4-8}$-alkyle group where alkyl is defined above. Examples of alkylene groups are —(CH$_2$)—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—.

The term "$C_{4-12}$-alkenylene" refers to a divalent $C_{4-12}$-alkenyl of formula —(CH$_2$)$_x$—(CH=CH)$_y$—(CH$_2$)$_z$— wherein x and z are, independently, 0, 1, 2, 3, 4, 5, 6, 7 or 8 and y is 1, 2, 3 or 4. Similarly, the term "$C_{4-8}$-alkenylene", refers to a divalent $C_{4-8}$-alkenyl. Examples of alkenylene groups include butenyl, pentenyl, pentadienyl, hexenyl, hexadienyl, heptenyl, heptadienyl, octenyl, octadienyl, nonenyl, nonadienyl, decenyl, decadienyl, undecenyl, undecadienyl, undodecenyl, undodecadienyl, and their straight-chain and branched and stereo-isomers.

The term "$C_{3-6}$-cycloalkyl" refers to a saturated or partially unsaturated cyclic hydrocarbon group having 3 to 6 (inclusive) carbon atoms. This term is further exemplified by groups as cyclopropyl, cyclobutyl, cyclopentyl, and cyclohexyl. The "$C_{3-6}$-cycloalkyl" group can optionally be mono-, di-, tri- or multiply-substituted by a halogen as defined below, a $C_{1-4}$-alkyl group as defined above, a —NH$_2$, a —NH—CO$_2$H, a NH—CO—R$^a$, —CO$_2$H, —NHR$^a$ and/or —NR$^a$R$^b$ wherein R$^a$ and R$^b$ are independently a $C_{1-4}$-alkyl group as defined above.

The term —(CH$_2$)—$C_{3-6}$-cycloalkyl group refers to a —CH$_2$— substituted $C_{3-6}$-cycloalkyl group wherein the cycloalkyl group is as defined above.

The term "$C_{6-10}$ aryl" refers to a monocyclic or bicyclic aromatic ring system of 6 to 10 (inclusive) carbon atoms, preferably 6 carbon atoms. This term is further exemplified by groups as phenyl and naphtyl. The $C_{6-10}$-aryl group can optionally be mono-, di-, tri- or multiply-substituted by a halogen as defined below and/or a $C_{1-4}$-alkyl group as defined above.

The terms "halo" or "halogen" refers to fluorine, chlorine, bromine and iodine.

The term "halogen-$C_{1-4}$-alkyl", refers to a halogen substituted $C_{1-4}$-alkyl group wherein both halogen and alkyl groups have the meaning as above. Preferred "halogen-$C_{1-4}$-alkyl" groups are fluorinated "halogen-$C_{1-4}$-alkyl" groups such as —$OF_3$, —$CH_2$—$CF_3$, —$CH(CF_3)_2$, —$CH(CH_3)(CF_3)$, —$C_4F_9$.

The term "$C_{1-12}$-alkoxy" refers to a branched or straight-chain monovalent saturated aliphatic hydrocarbon group of 1 to 12 (inclusive) carbon atoms attached to an oxygen atom. Similarly, the terms "$C_{1-8}$-alkoxy", "$C_{1-5}$-alkoxy", "$C_{1-4}$-alkoxy", "$C_{1-2}$-alkoxy" refer to branched or straight-chain monovalent saturated aliphatic hydrocarbon groups of, respectively, 1 to 8 (inclusive), 1 to 5 (inclusive), 1 to 4 (inclusive), 1 to 2 carbon atoms. Examples of "alkoxy" groups are methoxy, ethoxy, propoxy, butoxy, pentoxy, hexyloxy, heptyloxy, octyloxy, and their branched isomers.

The term "$C_{5-10}$-heteroaryl" refers to a heterocyclic aryl group containing 1 to 3 heteroatoms in the ring with the remainder being carbon atoms. In the said heterocyclic aryl group, suitable heteroatoms include, without limitation, sulfur and nitrogen. Exemplary heteroaryl groups include indolyl, azaindolyl, thiophenyl, benzothiophenyl, thioazolyl, benzothiazolyl. The heteroaryl group can optionally be mono-, di-, tri- or multiply-substituted by a halogen and/or a $C_{1-4}$-alkyl group, as defined above. When the heteroaryl group is mono-, di-, tri- or multiply-substituted by a $C_{1-4}$-alkyl group, said alkyl group is preferably a methyl group.

The term "polyether ring", refers ring containing 1, 2, or 3 ether groups, an ether group being an oxygen atom connected to two alkyl groups as defined above The term "lactone" refers to a closed ring containing an oxygen atom adjacent to a carbonyl group (—CO—O—). It can be considered as the condensation product of an OH group with a $CO_2H$ group.

The term "lactam" refers to a closed ring containing an nitrogen atom adjacent to a carbonyl group (—CO—NH— or —CO—NR— with R being for example an alkyl group as defined above).

The terms "substituted" and "substitution and the like", refer to the replacement of one, two, three or more atoms in a given group by one, two, three or more suitable substituents, including, without limitation, a halogen, a $C_{6-10}$ aryl group, a $C_{1-4}$-alkyl group, a $C_{1-2}$-alkyl group, a $C_{1-2}$-alkoxy group, a $NH_2$, a NH—CO—$R^a$, —$CO_2H$, —$NHR^a$ and/or —$NR^aR^b$ wherein $R^a$ and $R^b$ are independently a $C_{1-4}$-alkyl group, or a mixture of those substituents.

In some embodiments of the invention, the compounds of the invention can contain one or more asymmetric centers and thus occur as racemates and racemic mixtures, single enantiomers, individual diastereoisomeric mixtures. All such isomeric forms of these compounds are included in the present invention, unless expressly provided otherwise.

In some embodiments, the compounds of the invention can contain one or more double bonds and thus occur as individual or mixtures of Z and/or E isomers. All such isomeric forms of these compounds are included in the present invention, unless expressly provided otherwise.

In the embodiments where the compounds of the invention can contain multiple tautomeric forms, the present invention also includes all tautomeric forms of said compounds unless expressly provided otherwise.

In the embodiment where $R^{7a}$ together with $R^6$ form a lactone or a polyether ring,
$R^{7a}$ is $C_{4-12}$-alkylene, preferably $C_{4-8}$-alkylene group, and is linked to a —CO—O— or to a —O— functional group in $R^6$, or $R^{7a}$ is $C_{4-12}$-alkenylene, preferably $C_{4-8}$-alkenylene group, and is linked to a —CO—O— or to a —O— functional group in $R^6$.

In the embodiment where $R^{7b}$ together with $R^6$ form a lactam, $R^3$ is a —$(CH_2)_q$—CO—$NHR^{7b}$ and $R^{7b}$ is —$(CH_2)_{q'}$—NH— with q' being 2, 3, 4, 5, 6, 7 or 8.

In the embodiment where $R^9$ together with $R^6$ form a lactam, $R^3$ is a —$(CH_2)_qNHR^9$ and $R^9$ is a direct link between —$(CH_2)_qNH$— and a —CO— functional group in $R^6$.

In the embodiment where $R^8$ together with $R^6$ form a lactone or a polyether ring:
$R^8$ is $C_{4-12}$-alkylene, preferably $C_{4-8}$-alkylene group, and is linked to a —CO—O— or to a —O— functional group in $R^6$, or $R^8$ is $C_{4-12}$-alkenylene, preferably $C_{4-8}$-alkenylene group, and is linked to a —CO—O— or to a —O— functional group in $R^6$.

The terms "β ring", "β protein" or "β clamp" herein designate the β subunit of a eubacterial DNA polymerase III, such as that of *E. coli*. The β subunit of DNA polymerase III of *E. coli* is in particular described in Kong, X. P., Onrust, R., O'Donnell, M. & Kunyan, J. (1992). *Three-dimensional structure of the beta subunit of E. coli DNA polymerase III holoenzyme: a sliding DNA clamp.* Cell 69, 425-37.

According to an embodiment, P2 has the following formula (IV):

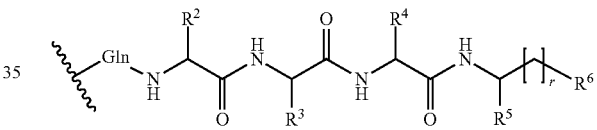

wherein $R^2$, $R^3$, $R^4$, $R^5$, $R^6$, and r are as defined above in formula (III).

Preferably, in formula (IV), r=0.

According to an embodiment, P2 has the formula (III), wherein $R^2$ is a —$(CH_2)$—$C_{3-6}$-cycloalkyl group.

According to an embodiment, P2 has the formula (III), wherein $R^2$ is a methylcyclohexane —$(CH_2)$—$C_6H_{11}$ group.

According to an embodiment, P2 has the formula (III), wherein:
$R^3$ is selected in the group consisting of a $C_{1-8}$-alkyl group, the side chain of arginine or lysine, —$(CH_2)_q$—$CO_2R^{7a}$, —$(CH_2)_q$—CO—$NHR^{7b}$, —$CH_2OR^8$ and —$(CH_2)_qNHR^9$, wherein q is 1, 2, 3 or 4, $R^{7a}$ is a hydrogen atom or a $C_{1-8}$-alkyl group, $R^{7b}$ is a hydrogen atom or a $C_{1-8}$-alkyl group, $R^8$ is a hydrogen atom or a $C_{1-8}$-alkyl group, $R^9$ is a hydrogen atom; and $R^6$ is —COOH, —$COOR^{10}$, —CO—$NH_2$, —CO—$NHR^{10}$, —$OR^{10}$ when r is 1 or 2, —NH—CO—$NHR^{10}$ when r is 1 or 2, wherein $R^{10}$ is a $C_{1-8}$-alkyl group optionally substituted by a $C_{6-10}$-aryl group; a $C_{3-6}$-cycloalkyl group; a $C_{6-10}$-aryl group optionally substituted by a halogen, a $C_{1-2}$-alkyl group and/or a $C_{1-2}$-alkoxy group.

Preferably, P2 has the formula (III), wherein:
$R^3$ is selected in the group consisting of the side chain of arginine, the side chain of lysine, —$(CH_2)_q$—$CO_2R^{7a}$, and —$(CH_2)_q$—CO—$NHR^{7b}$, wherein
q is 1, 2, 3 or 4,
$R^{7a}$ is a hydrogen atom or a $C_{1-8}$-alkyl group, and
$R^{7b}$ is a hydrogen atom or a $C_{1-8}$-alkyl group.

According to an embodiment, in formula (III), $R^4$ is a $C_{1-5}$-alkyl group or a $C_{1-2}$-alkyl group optionally substituted by a $C_{3-6}$-cycloalkyl group.

Preferably, in formula (III), $R^5$ is a —$(CH_2)$—$C_{6-10}$-aryl group optionally substituted by a halogen, a $C_{1-2}$ alkyl group and/or a $C_{1-2}$ alkoxy group.

Preferably, in formula (III), $R^6$ is —COOH or —CO—$NH_2$.

According to an embodiment, P2 is chosen from the following peptides: $(Arg)_n$-Gln-Leu-Val-Leu-Gly-Leu-OH, $(Arg)_n$-Gln-Cha-Asp-Leu-Phe-OH, Cha representing cyclohexylalanine, $(Arg)_n$-Gln-Cha-Asp-Leu-pMePhe-OH, Gln-Cha-Asp-Leu-pClPhe-OH, $(Arg)_n$-Gln-Cha-Asp-Leu-3,4-$Cl_2$Phe-OH, and $(Arg)_n$-Gln-Cha-Asp-Leu-pBrPhe-OH (n being 0 or 1).

According to an embodiment, P2 is chosen from the following peptides: $(Arg)_n$-Gln-Cha-Asp-Leu-Phe-OH, Cha representing cyclohexylalanine, $(Arg)_n$-Gln-Cha-Asp-Leu-pMePhe-OH, Gln-Cha-Asp-Leu-pClPhe-OH, $(Arg)_n$-Gln-Cha-Asp-Leu-3,4-$Cl_2$Phe-OH, and $(Arg)_n$-Gln-Cha-Asp-Leu-pBrPhe-OH (n being 0 or 1).

The present invention also relates to a medicament comprising a fusion peptide as defined above, preferably a fusion peptide having the formula (I) as defined above.

The present invention also relates to a pharmaceutical composition comprising a fusion peptide as defined above, preferably a fusion peptide having the formula (I) as defined above, in association with a pharmaceutically acceptable vehicle.

While it is possible for the compounds of the invention to be administered alone it is preferred to present them as pharmaceutical compositions. The pharmaceutical compositions, both for veterinary and for human use, useful according to the present invention comprise at least one fusion peptide having formula (I) or (II) as above defined, together with one or more pharmaceutically acceptable carriers and optionally other therapeutic ingredients.

In certain preferred embodiments, active ingredients necessary in combination therapy may be combined in a single pharmaceutical composition for simultaneous administration.

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The pharmaceutical compositions can be administered in a suitable formulation to humans and animals by topical or systemic administration, including oral, rectal, nasal, buccal, ocular, sublingual, transdermal, rectal, topical, vaginal, parenteral (including subcutaneous, intra-arterial, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Total daily dose of the compounds of the invention administered to a subject in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The present invention also relates to the fusion peptide as defined above for use as an antibacterial agent.

The present invention also relates to the fusion peptide as defined above for use for the treatment of bacterial infections. According to an embodiment, the bacterial infections are caused by Gram negative pathogens. Preferably, said bacterial infections are caused by bacteria belonging to the following bacteria families: Enterobacteriaceae, Pseudomonadaceae, Burkholderiales, Neisseriaceae, Campylobacterales, and Francisellaceae.

According to an embodiment, said bacterial infections are caused by bacteria selected from the group consisting of: bacteria from the genus *Escherichia* sp, in particular *E. coli*; bacteria from the genus *Klebsiella* sp, in particular *K. pneumoniae*; bacteria from the genus *Shigella* sp., in particular *S. sonnei*, *S. dysenteriae*, and *S. flexneri*; bacteria from the genus *Salmonella* sp., in particular *S. enterica*, *S. typhi*, and *S. parathyphi*; and bacteria from the genus *Yersinia* sp., in particular *Y. enterocolitica* and *Y. pestis*.

According to an embodiment, said bacterial infections are caused by bacteria selected from the group consisting of: bacteria from the genus *Acinetobacter* sp, in particular *A. baumannii*; and bacteria from the genus *Pseudomonas* sp., in particular *P. aeruginosa*.

According to an embodiment, said bacterial infections are caused by bacteria selected from the group consisting of: bacteria from the genus *Burkholderia* sp, in particular *Burkholderia cepacia*.

According to an embodiment, said bacterial infections are caused by bacteria selected from the group consisting of: bacteria from the genus *Neisseria* sp, in particular *N. gonorrhoeae* and *N. meningitidis*.

According to an embodiment, said bacterial infections are caused by bacteria selected from the group consisting of: bacteria from the genus *Campylobacter* sp, in particular *C. jejuni*.

According to an embodiment, said bacterial infections are caused by bacteria selected from the group consisting of: bacteria from the genus *Francisella* sp., in particular *Francisella tularensis*.

According to an embodiment, the infections according to the invention are chosen from infections caused by multidrug resistant (MDR) bacteria, extensively drug-resistant (XDR) bacteria or pandrug-resistant (PDR) bacteria, derived from the above bacteria.

According to an embodiment, the infections according to the invention are chosen from infections caused by antibiotic-resistant bacteria, in particular with carbepenem resistance, cephalosporin resistance, or fluoroquinolone resistance. Such antibiotic-resistant bacteria are in particular mentioned in the WHO website (http://www.who.int/medicines/publications/WHO-PPL-Short_Summary_25Feb-ET_NM_WHO.pdf?ua=1).

According to an embodiment, the bacterial infections are selected from the group consisting of the following infections: respiratory infections, stomach infections, gastrointestinal infections, blood infections, skin infections, bladder infections, kidney infections, urinary tract infections, ear infections, eye infections, and meningial infections. A skin infection may include an infection of a mucosal membrane, such as the oral cavity, oesophagus or eye, e.g. cornea.

In the context of the invention, the term "treating" or "treatment", as used herein, means reversing, alleviating, inhibiting the progress of, or preventing the disorder or condition to which such term applies, or one or more symptoms of such disorder or condition.

FIGURES

FIG. 1 concerns the analysis of peptide penetration into *E. coli* cells. (a) Fluorescence microscopy of *E. coli* cells exposed to the three different FITC labeled peptides. (b) The average FITC signals generated by more than 100 bacteria for each peptide were compared and results are represented as a boxplot. ANOVA analysis of the data set confirms that $P_{122}$ (FITC-Py) penetrates on average about 3 times more efficiently than either $P_{72}$ (FITC-Py-P7Scr) or $P_{150}$ (FITC-Py-P7) (***P<0.000001).

Figure 2:
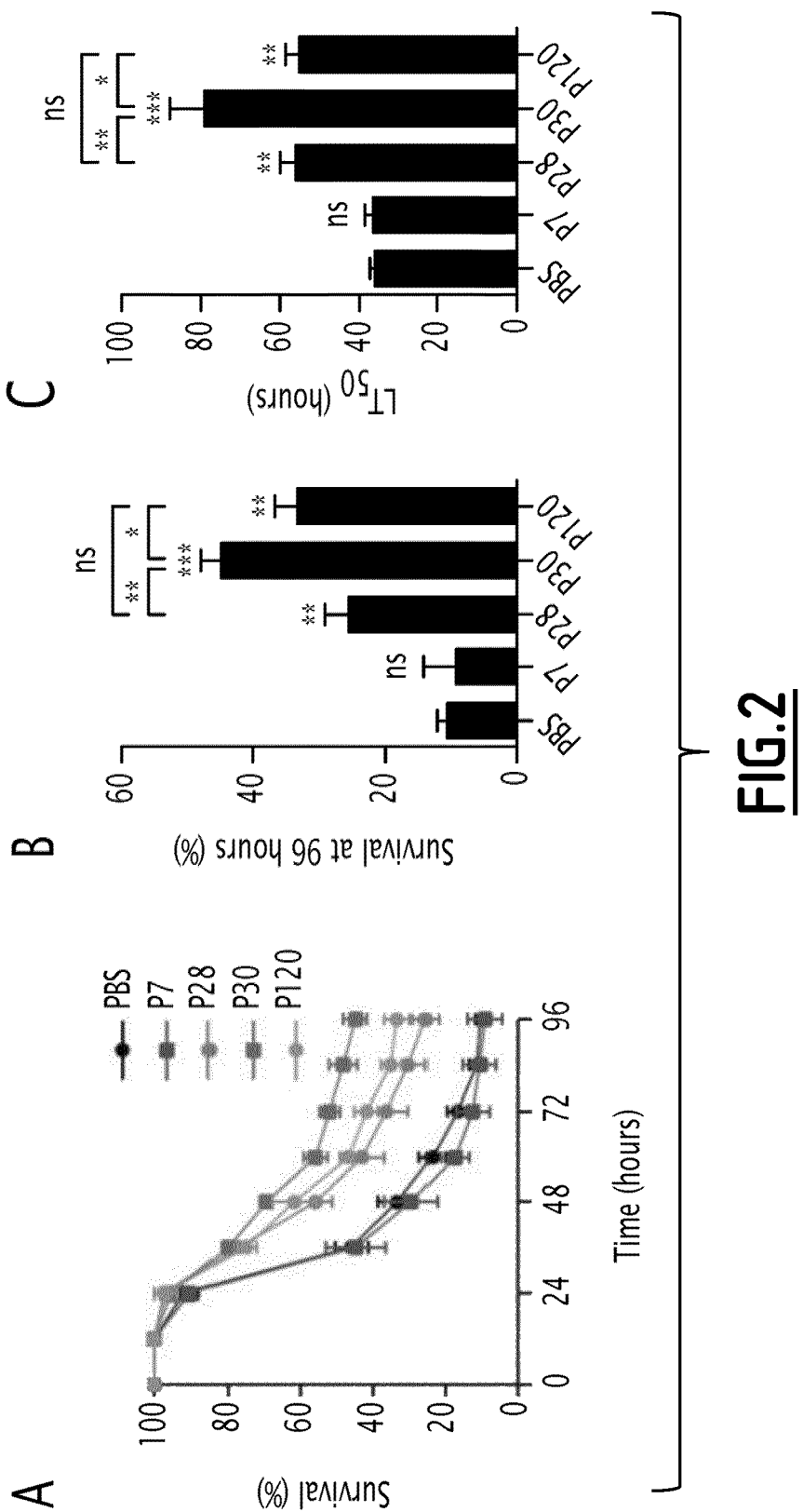

FIG. 2 concerns the in vivo survival assay using *Drosophila melanogaster* infection model. Seven-day-old female kenny$^{C02831}$ flies were infected by septic injury with a thin tungsten needle previously dipped in an *E. coli* suspension diluted in PBS and kept at 29° C. 1 and 24 hours after infection, 18.4 nl of peptides (1 mM) diluted in PBS or PBS alone were injected into the flies body cavity. (A) Survival curves. (B) Survival rate after 96 hours. (C) Lethal time 50% (LT50). Data represent means±standard errors of at least 3 independent experiments, each containing three groups of 20 flies. One-Way ANOVA test: *P<0.05, P<0.01, *P<0.001. ns: non-significant (P28: Onc112; P30: Onc112-P7; P120: Onc112-P7Scr).

Figure 3:
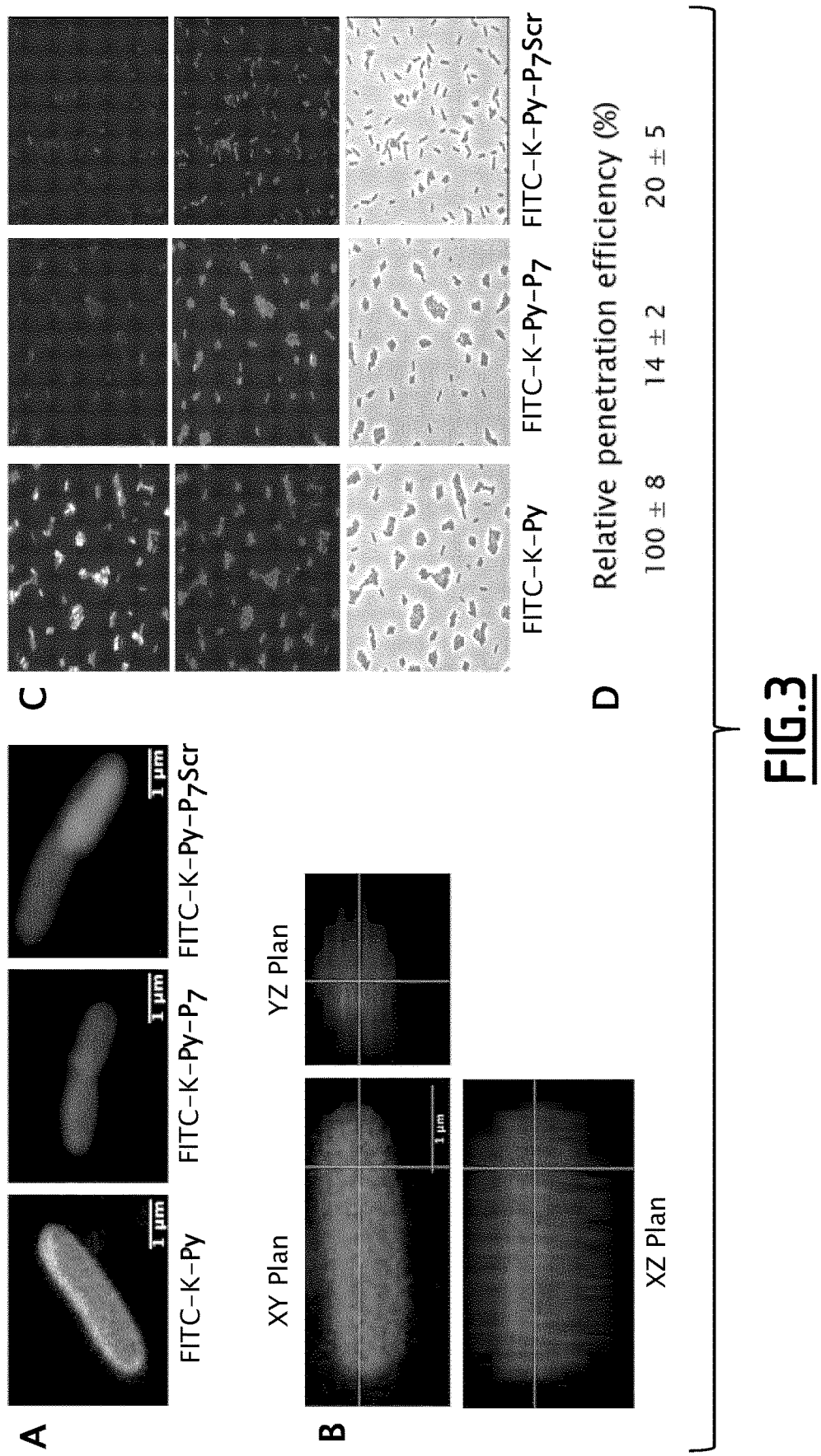

FIG. 3 concerns the analysis of peptide penetration into *E. coli* cells. (A) Confocal LSM of D22 *E. coli* cells exposed to the three different FITC labeled peptides (9 µM) and stained with Nile Red. Composite image were obtained by merging the FITC (colored in dark grey) and Nile Red (colored in light grey) channels and clearly show the cytoplasmic localization of FITC. (B) Three dimensional analysis of the FITC-K-Py (9 µM) peptide penetration in the bacterial cytoplasm. D22 cells were treated as in A, except that they were additionally stained with DAPI. It clearly appears that the two fluorescent signals from DAPI and FITC are located within the cell, while Nile Red stains the lipidic phases of membranes. This unambiguously indicates that the fluorescent peptide is transported into the cytoplasm. (C) Representative fluorescent microscopy images of D22 *E. coli* cells exposed to the three different FITC labeled peptides (9 µM) and stained with DAPI. Fusion peptides are less efficiently uptaken than FITC-K-Py. (D): Relative FITC fluorescence quantification (average±SD) normalized to that measured with FITC-K-Py peptide.

Figure 4:
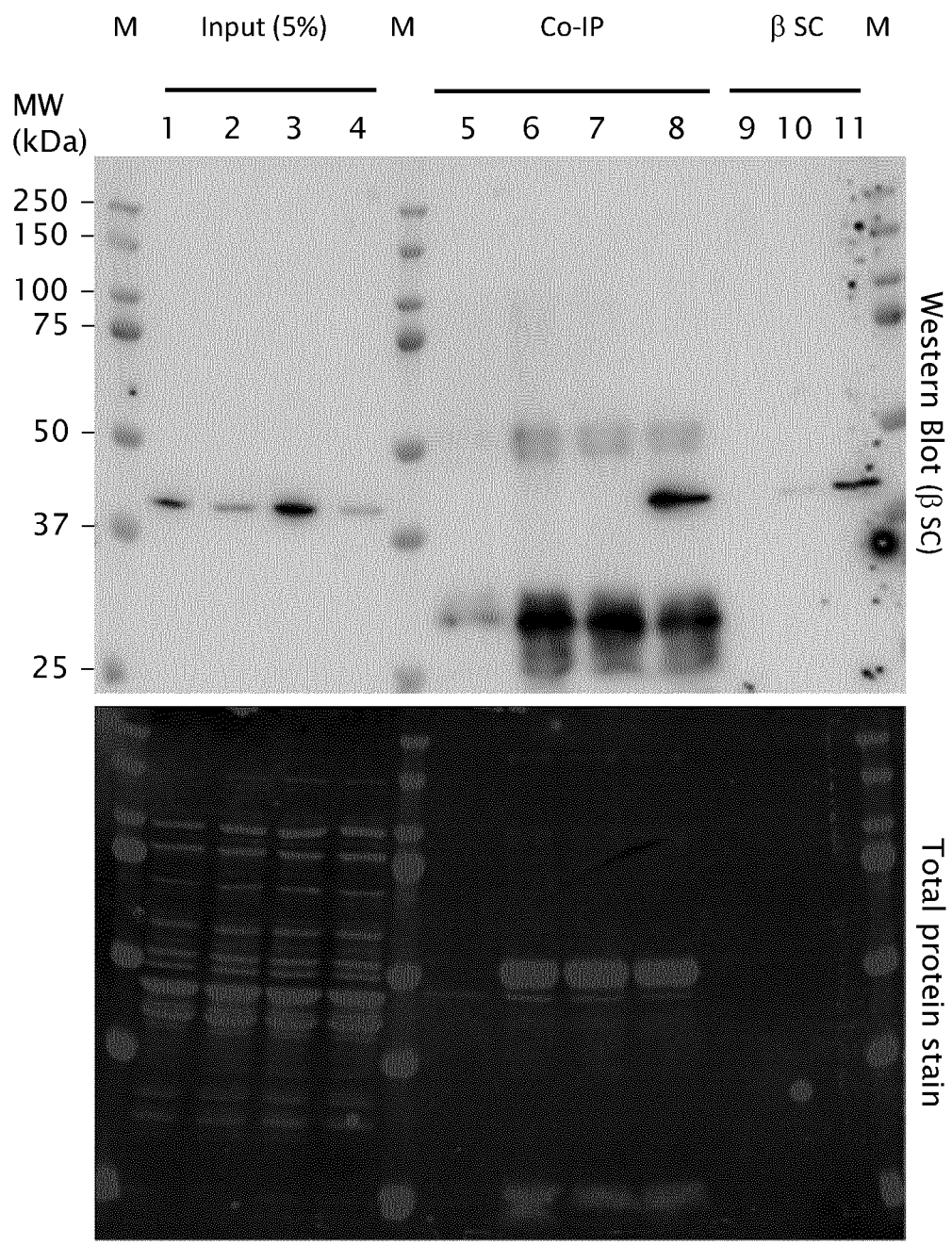

FIG. 4 concerns the co-immunoprecipitation of FITC-K-Py-P$_7$ peptide with the E *coli* β SC. *E. coli* D22 cells were incubated for 1 hour with or without 16 µM of the indicated FITC labelled peptide (lanes 1 and 5: no peptide; lanes 2 and 6: FITC-K-Pyr; lanes 3 and 7: FITC-K-Py-P7Scr; lanes 4 and 8: FITC-K-Py-P7). Lanes 1-4: 5% of the pre-cleared extracts were loaded as input controls. Lanes 5: Ig G sepharose beads pull down of the pre-cleared extracts not exposed to anti-FITC antibody. Lanes 6 to 8: Ig G sepharose beads pull down of the pre-cleared extracts previously incubated with FITC-labelled peptides and then exposed to anti-FITC antibody. Lanes 9-11: purified native β SC protein (lane 9: 5 ng; lane 10: 10 ng; lane 11: 20 ng). Upper image: western blot using the Ab 246, β SC specific monoclonal antibody. Lower image: total protein staining of the same membrane. M: Molecular weight markers.

EXAMPLES

The present invention is based on the combination of the P7 peptide with two PrAMPS, Onc112 (Knappe, D., Piantavigna, S., Hansen, A., Mechler, A., Binas, A., Nolte, O., Martin, L. L., and Hoffmann, R. (2010). *Oncocin (VDKPPYLPRPRPPRRIYNR-NH2): a novel antibacterial peptide optimized against gram-negative human pathogens.* J Med Chem 53, 5240-5247; Knappe, D., Zahn, M., Sauer, U., Schiffer, G., Strater, N., and Hoffmann, R. (2011). *Rational design of oncocin derivatives with superior protease stabilities and antibacterial activities based on the high-resolution structure of the oncocin-DnaK complex.* Chembiochem 12, 874-876) and unglycosylated pyrrhocoricin (Py) (Hoffmann, R., Bulet, P., Urge, L., and Otvos, L., Jr. (1999). *Range of activity and metabolic stability of synthetic antibacterial glycopeptides from insects.* Biochim Biophys Acta 1426, 459-467; Taniguchi, M., Ochiai, A., Kondo, H., Fukuda, S., Ishiyama, Y., Saitoh, E., Kato, T., and Tanaka, T. (2016). *Pyrrhocoricin, a proline-rich antimicrobial peptide derived from insect, inhibits the translation process in the cell-free Escherichia coli protein synthesis system.* J Biosci Bioeng 121, 591-598), to form two fusion peptides, $P_{30}$ and $P_{116}$ respectively.

Beside their own antibacterial effect, the PrAMPS serve as Trojan horses and transport $P_7$ into the cell where each peptides will be able to bind to its respective intracellular target.

Material and Methods

Peptides Synthesis.

Pyrrhocoricin (Py) was purchased at Novopro (Shangai, China). Mass spectrometry analysis of Py was performed using an Autoflex III apparatus (Brucker).

Commercially available reagents were used throughout without purification. N,N-dimethylformamide (DMF, peptide synthesis-quality grade) was purchased from Carlo Erba, and piperidine and trifluoroacetic acid (TFA) were purchased from Alfa Aesar. Rink amide PS or Wang resin was purchased from MerckMillipore. 0-(Benzotriazol-1-yl)-N,N,N',N'-tetramethyluronium hexafluorophosphate (HBTU), N, N'-diisopropylcarbodiimide (DIC) and (Benzotriazol-1-yloxy)tris(dimethylamino) phosphonium hexafluorophosphate (BOP) and all standard N-Fmoc-protected L- and D-amino acids were purchased from Iris Biotech. N,N-Diisopropylethylamine (DIEA) and 5(6)-Carboxyfluorescein (FITC) were purchased from Sigma-Aldrich. Peptides were synthesized on solid support from a fully automated microwave peptide synthesizer: Liberty Blue System synthesizer (CEM Corporation). RP-HPLC-quality acetonitrile ($CH_3CN$, Sigma-Aldrich) and MilliQ water were used for RP-HPLC analyses and purification. Analytical RP-HPLC analyses were performed on a Dionex U3000SD with a Macherey-Nagel Nucleodur column (4.6× 100 mm, 3 μm) at a flow rate of 1 ml·min$^{-1}$ at 50° C. The mobile phase was composed of 0.1% (v/v) TFA-$H_2O$ (solvent A) and 0.1% TFA-$CH_3CN$ (solvent B). Purification was performed on a Gilson GX-281 with a Macherey-Nagel Nucleodur VP250/21 100-5 C18ec column (21×250 mm, 5 μm) at a flow rate of 20 mL·min$^{-1}$. LC-MS analyses were recorded in positive ion-mode with an ESI ion source on an Agilent™ Time-of-Flight MS mass spectrometer Model 6230 coupled with Agilent™ 1290 series front-end.

Peptides with an Amidated C-Terminus Such as $P_{28}$, Py and $P_{122}$

Peptides were synthesized using a Rink Amide PS resin with low loading (0.32 mmol·g$^{-1}$), Peptides with an Acid on C-Terminus Such as P30, P120, P116, P188, P150 and P72

Peptides were synthesized using a Fmoc-Phe-Wang resin with low loading (0.31 mmol·g$^{-1}$) or Wang resin with low loading (0.30 mmol·g$^{-1}$).

The attachment of the First Amino Acid on Wang Resin was performed from symmetrical anhydride method. 10.0 eq of Fmoc-amino acid (relative to resin loading) were dissolved in dry DCM with a minimum amount of DMF. The reaction mixture was cooled to 0° C. and 5.0 equiv of DIC (relative to resin loading) were slowly added to the amino acid solution. The mixture is stirred for 20 min at 0° C. and DCM was evaporated. The residue was dissolved in a minimum of DMF and added to the resin suspension followed by 0.1 equiv of DMAP (relative to resin loading). The suspension is shaken at room temperature for 2 h.

General Procedure for Peptide Synthesis

The standard SPPS methodology was applied with Fmoc/tBu protocol. Resin was placed into a reaction vessel and was allowed to swell using a mixture of DMF and DCM (50%, v/v) for 30 min. After swelling, peptides were synthesized with automated microwave by repetition of the following cycle conditions: 1) Fmoc deprotection performed with a solution of 20% piperidine in DMF in two steps: 30 and 180 s, both at 75° C., 100 W, and 2) and coupling reactions performed with 5.0 eq. (according to resin initial loading) of Fmoc amino acid (0.5 mmol, 2.5 mL of 0.2 M solution of DMF), 5 eq. of HBTU (0.5 mmol, 2.5 mL of 0.2 M solution in DMF) in presence of 10 eq. of DIEA (1 mmol, 0.5 mL of 2 M DMF solution). Each coupling of N-Fmoc-protected amino acid was performed twice and heated at 75° C. under MW irradiation: 30 W for 300 s.

Protocol for the On-the-Resin N-Terminal Fluorescent Probe Introduction for $P_{122}$, $P_{150}$ and $P_{72}$ 1) 8.0 eq. (according to resin initial loading) of a carboxy-derivative Fluorescein with 8.0 eq. of BOP were dissolved in DMF NMP was added dropwise until a homogeneous and limpid solution. Then, the reaction mixture was stirred with vigorous agitation at room temperature for 1 h.

2) Transfer the activated fluorescein solution into a syringe with the pre-swelled peptide-resin. Under vigorous agitation, DIEA was added dropwise, allowing complete homogenization between additions (usually 10-15 min). The reaction was then carried out for 48 h and after the peptide-resin was washed with DMF (×2), DCM (×3) and DMF (×2). Finally, a solution of 20% piperidine in DMF (v/v) added to the peptide-resin and stirred for 30 minutes.

After completion of the synthesis, the peptide resin was filtered and then washed with DMF (×2) and DCM (×3) before drying. The cleavage step and removal of the protecting groups were performed by treatment with 5 mL of a freshly prepared solution: TFA/TIS/$H_2O$ (95/2.5/2.5; v/v/v) and stirred for 4 h at room temperature. The resin was then filtered off, and the filtrate was concentrated under reduced pressure. The crude peptide was precipitated as TFA salts using cold $Et_2O$ (z 20 mL). The precipitate was recovered by centrifugation, dissolved in a mixture of ACN/$H_2O$ and freeze dried. Finally, the solid crude was dissolved in mixture of ACN/$H_2O$ with minimum of ACN and purified with the appropriate gradient on semi-preparative RP-HPLC.

Bacterial Strains.

E. coli strain D22 (F-, IpxC101, proA23, lac-28, tsx-81, trp-30, his-51, tufA1, rpsL173(strR), ampCp-1 was purchased at E. coli Genetic Stock Center (Yale University) and used in the determination of MIC and in the peptide penetration assays. E. coli ATCC23724 cells were used to infect D. melanogaster flies. 70S ribosomes were purified from the E. coli MRE600 strain (Accession AY140951) and BL21 (DE3) pLys strain was used for production of the DnaN protein.

Production of E. coli 70S Ribosome Particles.

E. coli MRE600 cells were grown at 37° C. in LB medium until OD$^{600}$=1. Cells were centrifuged at 4° C., and pellets were resuspended in buffer A (20 mM Tris HCl pH 7.5; 200 mM $NH_4Cl$; 20 mM $MgCl_2$; 0.1 mM EDTA; 6 mM β-mercaptoethanol) and lysed using a French press at 1.6 kbar. The crude lysate was centrifuged (18 200 rpm) for 30 mn at 4° C. The supernatant was further centrifuged (47000 rpm) at 4° C. for 4 hours and the pellet resuspended in 12.5 ml of buffer A. This solution was laid on a 30% sucrose cushion and centrifuged (34 000 rpm) for 19 hours at 4° C. The ribosome pellet was resuspended in 12.5 ml buffer B (20 mM Tris HCl pH 7.5; 50 mM $NH_4Cl$; 10 mM $MgCl_2$; 0.1 mM EDTA; 6 mM β-mercaptoethanol) and centrifuged again (18 200 rpm) for 1 hour at 4° C. The supernatant was concentrated on Centrikon 100K (Millipore) and washed extensively with ITC 70S buffer. Ribosome concentration was determined by UV absorption at 260 nm. Samples were snap frozen in liquid nitrogen and kept at −80° C.

Production and Purification of E. coli Sliding Clamp.

The DnaN protein was expressed from plasmids pET15b, containing the dnaN gene from E. coli, transfected in BL21 (DE3) pLys E. coli strain. Cells were grown in LB at 37° C. to OD 0.5, then induced by IPTG (0.1 mM) at 28° C. overnight. DnaN protein was first enriched on a Ni-NTA column, eluted with an imidazole step (300 mM) and further purified on a Source Q column in buffer containing 20 mM Tris HCl pH 7.5, 0.5 mM EDTA and 10% glycerol, using a gradient from 0 to 0.5 M NaCl. After a final ultracentrifugation (45K, 1 h, 20° C.), soluble proteins were concentrated on a Centricon 30K (Millipore) in the same buffer and stored at 4° C. in 2 M ammonium sulfate.

Isothermal Titration Calorimetry (ITC) Experiments.

ITC experiments were performed on a iTC$_{200}$ (Microcal Malvern Panalytical) or PEAQ-ITC instrument (Microcal Malvern Panalytical). The E. coli SC were washed extensively with ITC buffer (R1 buffer: 10 mM Hepes pH 7.4, 0.15 M NaCl, 3 mM EDTA) on Centrikon 10K at 4° C. before ITC experiments. DLS analysis shows that the protein solution is monodisperse (data not shown). Similarly, E. coli 70S ribosome particles were also washed extensively with ITC 70S buffer (50 mM Tris HCl pH7.5, 30 mM KCl, 70 mM NH$_4$Cl, 7 mM MgCl$_2$, 1 mM DTT, 5% glycerol) on Centrikon 100K at 4° C. before ITC experiments. Peptides (100 to 400 µM) were titrated at 30° C. (303.15 K) in sequential injections (usually 2 µl each) into a SC (20 or 30 µM) or 70S (10 to 15 µM) solution. Data were corrected from control experiments in which peptides were injected in ITC buffer solution. Each titration was performed at least twice. Analyses of experimental data were performed with AFFINImeter software (https://www.affinimeter.com; S4S, Santiago de Compostela, Spain). All thermodynamic data are provided in Table 2.

Microdilution Broth Assays.

E. coli strains were cultivated on either agar or liquid 1× Mueller Hinton broth unless specified. MIC assays were performed in duplicate in 96-well microtiter plates on the basis of the protocol recommended by the Clinical and Laboratory Standards Institute. Briefly, a mix of 5-6 fresh (less than 36 hours) colonies grown on MH agar plates were inoculated in 3 ml of MH broth and incubated for about 16 h at 37° C. under agitation. 30 µl of this saturated culture were inoculated in 3 ml of fresh medium and allowed to grow until OD$_{600}$ nm of about 0.6-0.8. Dilution to an OD$_{600}$ nm of 0.002 was made in MH broth. Within a time laps not exceeding 30 min, 50 µl of this cell suspension was added to 50 µl of MH broth (containing or not the peptide/antibiotic diluted in MH broth) in wells of a 96-well round bottom microwell plate (Greiner; final cell density about 2 to 5×10$^5$ cfu/ml). Plates were incubated at 37° C. for 18-24 h and final turbidity of each well was measured at 620 nm using a Multiskan FC microplate reader (Thermo Scientific). MIC was defined as the minimal antibiotic concentration that result in no increase of turbidity at that time. Each MIC determination was performed in duplicate and at least in two independent experiments. Plating of 75 µl of the content of the wells of interest on LB Agar plates was used to determine the MBC that is defined by a decrease of at least 99.9% of cell viability as compared to the number of viable cells in the inoculum (about 2 to 5×10$^4$ cfu).

Peptides Penetration Assays.

In order to analyse the penetration capacity of the peptides in E. coli D22 cells, FITC-labeled peptides were added to 1 ml of bacterial cultures (OD$_{600}$=0.8) at a final concentration of 8 µg/ml. The cells were allowed to acquire the peptides for 1 h at 37° C., washed 3 times with 0.5 ml PBS, fixed with 1% formaldehyde solution in PBS for 45 min at room temperature, washed 3 times with 0.5 ml PBS and finally resuspended in 50 µl PBS. Cells were visualized using a Leica DM5500 microscope equipped with a 100× objective and images were processed using Fiji software. One-way ANOVA statistical analysis was performed with the R package.

In Vivo Survival Assay Using a D. melanogaster Infection Model.

50 ml of E. coli ATCC23754 were grown at 29° C. in LB media up to exponential phase (OD$_{600}$=0.6-0.8) and centrifuged at 5.000 g for 5 min. The pellet was then diluted in 1 ml of PBS. Immune-deficient kenny$^{C02831}$ (Bou Aoun, R., Hetru, C., Troxler, L., Doucet, D., Ferrandon, D., and Matt, N. (2011). Analysis of thioester-containing proteins during the innate immune response of Drosophila melanogaster. J Innate Immun 3, 52-64) flies were raised at 25° C. with 60% humidity on standard cornmeal-agar medium. Seven-day-old female flies were infected by septic injury with a thin tungsten needle previously dipped in an E. coli suspension diluted in PBS and kept at 29° C. 1 and 24 hours after infection, 18.4 nl of peptides (1 mM) diluted in PBS or PBS alone were injected into the fly body cavity (Nanoject II apparatus; Drummond Scientific). Because log-rank analysis can only compare two survival curves at a time in the same experiment, we decided to compute the median lethal time 50 (LT50) and the survival rate at 96 hours to perform One-way ANOVA statistical analysis.

RESULTS

Peptides Chemical Synthesis.

Peptide P7 (AcQXDLF, X=cyclohexylalanyl, Cha) has been previously developed, according to a structure-based strategy (Wolff, P., Olieric, V., Briand, J. P., Chaloin, O., Dejaegere, A., Dumas, P., Ennifar, E., Guichard, G., Wagner, J., and Burnouf, D. Y. (2011). Structure-based design of short peptide ligands binding onto the E. coli processivity ring. J Med Chem 54, 4627-4637), for its increased interaction with $^{Ec}$SC. As compared to the original natural SC binding peptide (RQLVLGL) from the E. coli DNA polymerase IV, its affinity for the $^{Ec}$SC target shows a 50 fold increase, yielding a dissociation constant (K$_d$) of 400 nM at 30° C. Onc112 is derived from a natural oncocin from the Hemipteran Oncopeltus fasciatus, which has been modified to increase its stability. Pyrrhocoricin is another natural PrAMP from Pyrrhocoris apterus (Cociancich, S., Dupont, A., Hegy, G., Lanot, R., Holder, F., Hetru, C., Hoffmann, J. A., and Bulet, P. (1994). Novel inducible antibacterial peptides from a hemipteran insect, the sap-sucking bug Pyrrhocoris apterus. Biochem J 300 (Pt 2), 567-575). Both peptides interact within the PEC of Gram-negative bacteria 70S ribosomes, block the peptidyl transferase center and ultimately inhibit translation. Another intracellular target of PrAMPs, namely DnaK, was also identified but the PrAMP-DnaK interaction was not considered as the major molecular event responsible for bacterial growth inhibition.

Covalent fusion peptides joining P$_7$ and PrAMP peptides sequences were synthesized and it has been shown that the fusion peptides of the invention display a synergic antibacterial activity. N-terminal labeled FITC derivatives were also initially synthesized to follow the peptide penetration in bacterial cells. All peptides used in the examples are presented in Table 1.

Peptide Interactions with $^{Ec}$SC and $^{Ec}$70S.

The peptide interactions with their respective targets were monitored by ITC at 30° C. The interaction of P7 with $^{Ec}$SC is a spontaneous enthalpy driven process, as previously observed. The unfavorable entropic factor can be partly related to the loss of freedom degrees due to peptide binding. PrAMPs P28 and Py do not interact with $^{Ec}$SC. In contrast, the fusion peptides, resulting from the C-terminal addition of P$_7$ to each PrAMP, i.e. P$_{30}$ (Onc112-1$^3$$_7$) and P$_{116}$ (Py-P$_7$), interact with $^{Ec}$SC as efficiently as P7 alone, as shown by the similar thermodynamic profiles (Table 2 A).

TABLE 1

Peptides used in the examples.

| Name | | Sequence | Mw | Target |
|---|---|---|---|---|
| P7 | | Ac-QChaDLF-OH | 716.82 | $^{Ec}$SC |
| P28 | Onc112 | VDKPPYLPRPRPPRrlYNr-NH$_2$ | 2389.85 | 70S |
| P30 | Onc112-P7 | VDKPPYLPRPRPPRrlYNrNGPRQChaDLF-OH | 3472.08 | $^{Ec}$SC and 70S |
| P120 | Onc112-Scr | VDKPPYLPRPRPPRrlYNrNGPRChaFQLD-OH | 3472.08 | $^{Ec}$SC and 70S |
| Py | Pyrrhocoricin | VDKGSYLPRPTPPRPIYNRN-NH$_2$ | 2339.70 | 70S |
| P116 | Py-P7 | VDKGSYLPRPTPPRPIYNRNGPRQChaDLF-OH | 3307.82 | $^{Ec}$SC and 70S |
| P188 | Py-P7Scr | VDKGSYLPRPTPPRPIYNRNGPRChaGQLD-OH | 3307.82 | 70S |
| P122 | FITC_Py | FITC-KVDKGSYLPRPTPPRPIYNRN-NH$_2$ | 2826.17 | 70S |
| P150 | FITC-Py-P7 | FITC-KVDKGSYLPRPTPPRPIYNRNGPRQChaDLF-OH | 3794.30 | $^{Ec}$SC and 70S |
| P72 | FITC-Py-P7Scr | FITC-KVDKGSYLPRPTPPRPIYNRNGPRChaFQLD-OH | 3794.30 | 70S |

Cha: cyclohexylalanine.
r: (D)-R amino acid.
Scr: scramble.
FITC: fluorescein isothiocyanate.
Pyrrhocoricin was purchased from Novopro.
For all peptides the purity, as determined by HPLC (λ = 214 nm), was ≥98%.

However, these fusion peptides have a slightly increased affinity for $^{Ec}$SC as compared to P7 (Table 2 A), which may result from additional interactions established by PrAMPs or linker residues. Notably, the R residue of the linker (-GPR-; Table 1) of fusion peptides is observed in the natural $^{Ec}$SC binding peptide of DNA polymerase IV and was previously shown to establish interactions with $^{Ec}$SC residues, notably F$_{278}$. Other residues from the fusion peptides may interact at the surface of the clamp, thus contributing to their increased affinity for the target.

Control fusion peptides, P$_{120}$ (Onc112-P$_7$Scr) and P188 (Py-P$_7$Scr) were synthesized using a scrambled variant of P$_7$ (P$_7$Scr, XFQLD, X=cyclohexylalanyl, Cha). Both peptides fail to interact with $^{Ec}$SC, underlining the sequence specificity of the P$_7$ interaction within the $^{Ec}$SC pocket. The labeled fusion peptide P$_{150}$ (FITC-Py-P$_7$) similarly interacts with $^{Ec}$SC when compared to the unlabeled peptides (P$_7$ and P$_{116}$) (Table 2). However, the standard deviation observed between experiments is larger than for other P$_7$ derivatives, presumably because the presence of the FITC moiety somehow perturbs the stability of the P$_7$/SC complex. The two other fluorescent peptides, P$_{122}$ (FITC-Py) and P$_{72}$ (FITC-Py-P$_7$Scr) do not interact with $^{Ec}$SC (SI.1 H and J).

The interaction of each peptide with the $^{Ec}$70S ribosomal particle was also characterized by ITC (Table 2 B). For all peptides, the interaction with $^{Ec}$70S is an enthalpy driven process, presents an unfavorable entropic factor (–TΔS) that could be partly attributed to the loss of freedom degrees of the peptide upon binding in the 70S particle PEC, and a Gibb's free energy that ranges around –10 kcal/mole, indicating the spontaneous nature of the interaction (Table 2B). PrAMPs interact with high affinity with their target, with Kd in the order of 84 nM and 15 nM for Onc112 and Py, respectively. The affinity of Onc112 is fivefold lower than that measured for the natural PrAMP Py, probably because of the presence of the two D-arginines, as the increase in stability might have been selected at the expense of the affinity. The fusion peptides P$_{30}$ (onc112-P$_7$) and P$_{116}$ (Py-P$_7$) also efficiently interact with $^{Ec}$70S, almost similarly as the corresponding single peptides (Table 2B).

TABLE 2

A

| | P7 P7 | P28 Onc 112 | P30 Onc 112-P7 | P120 Onc 112-P7Scr | Py Py | P116 Py-P7 | P188 Py-P7Scr | P122 FITC-Py | P150 FITC-Py-P7 | P72 FITC-Py-P7Scr |
|---|---|---|---|---|---|---|---|---|---|---|
| ΔH (kcal/mole) | −13.7 ± 2.07 | Ni | −13.5 ± 0.46 | Ni | Ni | −13.9 ± 0.48 | Ni | Ni | −17.2 ± 4.53 | Ni |
| −TΔS (kcal/mole) | 4.71 ± 2.25 | Ni | 4.2 ± 04.8 | Ni | Ni | 4.3 ± 0.59 | Ni | Ni | 8.21 ± 5.0 | Ni |
| ΔG (kcal/mole) | −9.00 ± 0.19 | Ni | −9.28 ± 0.02 | Ni | Ni | −9.61 ± 0.11 | Ni | Ni | −8.99 ± 0.53 | Ni |
| Kd (nM) | 332 ± 124 | Ni | 205 ± 0.08 | Ni | Ni | 119 ± 22 | Ni | Ni | 390 ± 150 | Ni |

TABLE 2-continued

B

| | | P7 | P28 Onc112 | P30 Onc112-P7 | P120 Onc112-P7Scr | Py | P116 Py-P7 | P188 Py-P7Scr | P122* FITC-Py | P150* FITC-Py-P7 | P72* FITC-Py-P7Scr |
|---|---|---|---|---|---|---|---|---|---|---|---|
| ΔH (kcal/mole) | Ni | | −23.9 ± 4.1 | −25.6 ± 2.56 | −13 ± 2.27 | −19.2 ± 0.48 | −22.3 ± 3.82 | −15.4 ± 0.44 | −20.1 ± 13 | −13 ± 6.6 | −8.92 ± 0.2 |
| −TΔS (kcal/mole) | Ni | | 14.0 ± 4.3 | 15.7 ± 2.45 | 3.12 ± 2.9 | 8.23 ± 0.03 | 12 ± 3.76 | 5.5 ± 0.65 | 13.3 ± 13.2 | 6.7 ± 4.8 | 2.94 ± 0.2 |
| ΔG (kcal/mole) | Ni | | −9.82 ± 0.19 | −9.92 ± 0.11 | −9.85 ± 0.63 | −10.9 ± 0.52 | −10.3 ± 0.06 | −9.89 ± 0.2 | −6.91 ± 1.33 | −6.27 ± 0.23 | −5.98 ± 0.2 |
| Kd (nM) | Ni | | 84 ± 27 | 70.4 ± 12.7 | 101 ± 0.9 | 15.5 ± 11.9 | 37 ± 0.37 | 75.8 ± 25.8 | >10 µM | >10 µM | >10 µM |

A: peptides interaction with $^{Ec}$SC.
B: peptides interaction with $^{Ec}$70S.
All experiments were performed at 30° C. (303.15 K).
Data are means of at least two different experiments.
Ni: no specific interaction.
*: values not well defined because of the weak interaction due to the FITC moiety.

Although P28 and Py present similar thermodynamic profiles, indicating an overall similar mode of interaction, their respective thermodynamic values are significantly different (Table 2). This suggests some differences between peptide interactions within the PEC and correlate with structural data where 16 Py residues, but only 12 for $P_{28}$, are modeled in the Tth PEC, indicating that Py is more stable than $P_{28}$.

$P_7$ does not specifically bind to $^{Ec}$70S but some unspecific binding might be observed. When coupled to $P_{28}$ and $P_y$ to form the bi-functional peptides $P_{30}$ and $P_{116}$, the $P_7$ sequence does not affect the interaction of the PrAMPs with the ribosome (Table 2B). In fact, the differences in thermodynamic values observed between the parental peptides $P_{28}$ and Py are no longer observed when using the corresponding bi-functional peptides. This suggests that $P_7$ slightly contributes to the overall interaction of the bi-functional peptide in the PEC. In contrast, the enthalpic and entropic factor values drop dramatically for $P_{120}$ and $P_{188}$ peptides, suggesting that, when compared to $P_7$, the scrambled sequence affects the mode of interaction with 23S residues. This results in slightly smaller affinities for $P_{120}$ and $P_{188}$ than for other related peptides (Table 2B). Finally, the N-terminal FITC is highly deleterious for the interaction of Py and its derivatives with $^{Ec}$70S (Table 2B), indicating that this fluorescent moiety strongly hinders the PrAMP entry into the PEC. The poor interaction of these labeled peptides with $^{Ec}$70S precludes any serious analysis of the thermodynamic data.

In conclusion of these interaction studies, it has been shown that the fusion peptides ($P_{30}$ and $P_{116}$) resulting from the covalent addition of a $^{Ec}$SC binding peptide ($P_7$) at the C-terminal extremity of PrAMPs (Onc112 or Py, respectively) retain the binding characteristics of each parental peptide (Table 2), notably in terms of specificity. Indeed, fusion peptides are able to bind both targets, namely $^{Ec}$SC and $^{Ec}$70S, while their parental peptides are specific of a single one. Moreover, for all fusion peptides (but P120 and P188, bearing the scrambled sequence), similar thermodynamic profiles are observed, indicating that their mode of interaction with the target are comparable to those of their parental peptide. Finally, our experiments with FITC-labeled peptides reveal that the added moiety drastically affects the peptide interaction with $^{Ec}$70S, possibly by hindering entry into the PEC.

In Vitro Antibacterial Activity.

Antibacterial potency of the synthesized compounds was evaluated by the microdilution broth assay on the E. coli D22 strain (Table 3). $P_7$ alone fails to induce any detectable antibacterial activity. On the other hand, PrAMPs like Onc112 and Py demonstrate antibacterial activities in the micromolar range (1 µg/ml Onc112=0.41 µM; 8 µg/ml Py=3.4 µM), in agreement with previous reports which determined MIC values of 2 µg/ml (0.82 µM) and 9-18 µg/ml (3.69-7.56 µM) for Onc112 and Py, respectively. MBC determination for Py derived peptides confirms the bactericidal effect of these peptides, which appear as potent as ampicilin (Table 3).

When fusions of PrAMPs and $P_7$ (i.e. $P_{30}$ and $P_{116}$) were tested, no increase in the activity of the fusion peptides has been observed as compared to that obtained with the PrAMPs alone (compare MIC of $P_{30}$ to the one of $P_{28}$ and MIC of $P_{116}$ to the one of Py in Table 3).

TABLE 3

Antibacterial activities of the different peptides on E. coli D22 strain. Ampicillin and tetracyclin antibiotics were included in the assays as positive controls.

| Name | MIC$^a$ (µM) | MIC$^a$ (µg/ml) | MBC (µg/ml) |
|---|---|---|---|
| $P_7$ | >357 | >256 | n.d. |
| $P_{28}$: Onc112 | 0.21-0.42 | 0.5-1 | n.d. |
| $P_{30}$: Onc112-$P_7$ | 0.15-0.29 | 0.5-1 | n.d. |
| $P_{120}$: Onc112-Scr | 0.29-0.58 | 1-2 | n.d. |
| Py: Pyrrhocorricin | 0.85-3.4 | 2-8 | 8 |
| $P_{116}$: Py-$P_7$ | 1.2-2.4 | 4-8 | 8 |
| $P_{188}$: Py-$P_7$Scr | 1.2-2.4 | 4-8 | n.d. |
| $P_{122}$: FITC-Py | 181-362 | 512-1024 | n.d. |
| $P_{150}$: FITC-Py-$P_7$ | 16.9-33.8 | 64-128 | 128 |
| $P_{72}$: FITC-Py-$P_7$Scr | >269.9 | >1024 | n.d. |
| Ampicillin | 22.9-45.8 | 8-16 | 16 |
| Tetracyclin | 0.56-1.12 | 0.25-0.5 | 0.5 |

$^a$The range of MIC observed in a minimum of 2 independent experiments are indicated.

Eliminating or lowering the affinity of the fusion peptides toward the ribosome should allow the disclosure of the P7 antibacterial activity. To this end, the inventors took advantage of the N-terminal FITC labeling of the Py derived peptides that was shown to be deleterious to their ribosome binding capacities (Table 2B). The inventors first tested the bacterial cell penetration potential of these fluorescent peptides, as previously described for pyrrhocorricin. As shown in FIG. 1, comparison of the intensity of FITC staining of $E.$ $coli$ cells after exposure to equal amounts of $P_{122}$, $P_{150}$ or $P_{72}$ reveals that, although all three modified peptides actually penetrate $E.$ $coli$ cells, the fluorophore-tagged fusion peptides $P_{150}$ and $P_{72}$ enter the cells about 3 times less efficiently than $P_{122}$ (FIG. 1). Thus, the C-terminal, SC binding additional peptidic sequences in the $P_{150}$ and $P_{72}$ fusion peptides somehow prevent an optimal transport of the FITC labeled molecules within the bacteria. Then the MIC values were assessed for each of these modified peptides (Table 3). The strong decrease in antibacterial efficiency of $P_{122}$ (FITC-Py) as compared to Py (64 to 512 fold increase in MIC; Table 3) is directly in line with the measured decrease of the affinity of this molecule to its ribosomal target (Table 2B). The observed low antibacterial activity may be due either to residual binding to the ribosome or binding to the DnaK chaperone as described previously. When fusing $P_7$ to $P_{122}$, resulting in $P_{150}$, and despite a lower cell penetration capacity (FIG. 1), the MIC value drops by a factor 4 to 16. MBC determination for $P_{150}$ indicates a bactericidal mode of action of P7. Finally, a scrambled P7 sequence fused to $P_{122}$ does not show any cytotoxic effect at the highest concentration tested (1024 µg/ml; Table 3). These results definitively demonstrate that intracellular $P_7$ acts as an antimicrobial, bactericidal agent by interacting with $^{Ec}SC$.

In Vivo Infection Assay.

In order to further investigate the validity of our approach, the efficiency of the fusion peptide $P_{30}$ to control an in vivo infection was tested using $E.$ $coli$ sensitive $D.$ $melanogaster$ mutant flies. Onc112 derived peptides were used in this experiment because of their improved stability. The results are presented as survival curves (FIG. 2A). From these curves, the inventors derived the survival at 96 h after infection and the lethal time 50% ($LT_{50}$) (FIGS. 2B and C). Control peptides were $P_7$, $P_{28}$ and $P_{120}$. The survival curve obtained with P7 is similar to that obtained with the PBS control solution, indicating that the $P_7$ peptide has no effect on fly survival, in agreement with our previous observations that it does not have any antibacterial effect on in vitro $E.$ $coli$ cultures (Table 3; unpublished results). $P_{28}$ has a protective effect against $E.$ $coli$ infection as it induces a 2.5 fold increased survival of infected flies 96 h after injection (FIG. 2B). This is in line with the known in vivo antimicrobial activity of PrAMPs in murine infection models.

In contrast, $P_{30}$ increases the flies survival by a factor 4.5, indicative of a synergic effect of the fusion peptide as compared to the cumulative effects of $P_7$ and $P_{28}$. This synergic effect results from the combination of both the antimicrobial activity of the PrAMP component of $P_{28}$ and the interaction of $P_7$ with its cellular $^{Ec}SC$ target. This is confirmed by the activity of $P_{120}$, the control fusion peptide, which contains a $P_7$ scrambled sequence and interacts very weakly with $^{Ec}SC$ (Table 2A). The $P_{120}$ induced flies survival does not statistically differ from that measured with $P_{28}$. This indicates that the Py moiety of both peptides acts equally on their intracellular target and that the P7Scr moiety of P120 does not interfere with the $^{Ec}70S$ binding process in vivo. However, it is statistically different from that measured with $P_{30}$ (P<0.05) (FIGS. 2B and C), thus confirming that the increased survival observed with $P_{30}$ is related to the P7 activity.

The synergic effect of the fusion peptide $P_{30}$ on $E.$ $coli$ sensitive flies survival is even more clearly observed when considering the $LT_{50}$ curve (FIG. 2C). In this case, it appears that the integrated biological effect of $P_{30}$ is strongly different from that of $P_{28}$ and $P_{120}$.

Thus, the inventors have demonstrated for the first time the in vivo antimicrobial activity of a model SC binding peptide, namely $P_7$, both in bacterial cultures and using an $E.$ $coli$ infection assay in the fruit fly $D.$ $melanogaster$. Moreover, it has been shown that the combined action of two peptides simultaneously targeting the bacterial SC and the bacterial ribosome yields a synergistic antimicrobial effect in their in vivo infection model.

The antibacterial activity of the peptides was measured by defining their MIC in $E.$ $coli$. MIC values of 0.5 to 2 µg/ml were determined for Onc112 derived peptides, in close agreement with previous reports on Onc112 alone (2 µg/ml). A MIC value of 2-8 µg/ml was measured for Py and its derivatives, which is a slightly lower value than that measured previously for Py alone (9-18 µg/ml). The differences may be related to the different $E.$ $coli$ strains and/or culture media used in these studies. The higher activity of Onc112 relative to Py probably relies on its engineered increased stability. Regardless of the PrAMP fused to it, no $P_7$ related toxicity could be observed at this stage. However, a $P_7$ effect is readily observed when using the fluorescent peptides that do not, or barely, interact with the ribosome: although the MIC values are low as compared to those obtained with the unlabeled peptides, the fusion labeled peptide ($P_{150}$) induces a 4 to 16 times lower MIC value (64-128 µg/ml) than its related PrAMP ($P_{122}$) (512-1024 µg/ml), while the SC non-interacting control ($P_{72}$) is out of range (>1024 µg/ml). The fact that this specific P7 effect is not observed with unlabeled peptides may most probably be due to the difference in target concentration and affinities. Because of a target ratio ($^{Ec}70S$ vs $^{Ec}SC$) varying from 13 to 120 and a three times higher affinity of fusion peptides ($P_{30}$ and $P_{116}$) for the ribosome than for SC (Table 2), these bifunctional peptides preferentially interact with the $^{Ec}70S$, thus limiting the effect of the $P_7$ moiety. Blocking the peptide interaction with $^{Ec}70S$ by a N-terminal fluorophore redirects peptides toward the $^{Ec}SC$ target, thus revealing the toxic effect of the inhibition of the interactions between the SC and its natural partners.

The specific $P_7$ mediated effect is also observed in the fly survival test. The bi-functional peptide $P_{30}$ has a two times higher protective effect than its parental peptide $P_{28}$ on $E.$ $coli$ infected flies (FIG. 2). This effect is also similarly different from that of $P_{120}$ with a scrambled $P_7$ sequence, which is, as expected, identical to that measured for $P_{28}$. Surprisingly, the data of this test suggest that the two active parts of the bi-functional peptide equally contribute to the survival (FIG. 2). This result was not anticipated from ITC and MIC experiments and suggests that some other parameters modulate the accessibility of the targets in vivo. For example, differences in metabolic activity of the bacterial cells, between in vitro and in vivo situations, may greatly influence the numbers of ribosomal targets and differences in target accessibility may also depend on the translating status/activity of the cell, thus potentially reducing the contribution of the PrAMP moiety. Alternatively, in vivo modification(s) and further intracellular degradation of translocated peptides may dissociate the two active parts, thus fueling both the translation and the replication inhibition pathways.

This is the first demonstration of an in vitro and in vivo antibacterial activity of a SC binding molecule issued from a structure-based approach.

The present invention is thus based on the fact that peptides specifically designed to block the SC-DNA polymerases interaction and to inhibit the replicase activity readily induce cell death in bacterial cells cultures. Moreover, this bactericidal activity leads to a protective effect in living animals challenged by a bacterial infection. These results definitely validate SC as a molecular target for the development of a new class of antibiotics inhibiting bacterial replication. They also demonstrate that the use of the bifunctional antimicrobial agents presented here, selective for two different cellular targets involved in distinct and essential metabolic pathways, triggers a synergistic effect. Importantly, the results presented here disclose an efficient way to direct peptides targeting multiple aspect of the DNA metabolism. By its involvement in DNA replication and mutagenesis and its yet unexploited potential as antimicrobial target, the bacterial SC represents a major chance to develop antibiotics that may participate efficiently to the fight against antimicrobial resistance. Moreover, targeting simultaneously two distinct and essential metabolic pathways mathematically reduces the probability of resistance acquisition. Development of peptides to improve their stability, biological availability, bacterial cell delivery and efficiency in arresting major biochemical pathways is in progress.

Preparation and Activity of Other Fusion Peptides Labelled with FITC

Three other peptides were synthetized on the basis of the same preparation protocol as mentioned above.

These peptides are the followings:
CA3-124 (FITC-Onc112); CM1-92 (FITC-Onc112-P7) and CM1-94 (FITC-Onc112-P14)

| Name | Sequence |
| --- | --- |
| CA3-124 FITC-Onc112 | FITC-VDKPPYLPRPRPPRrlYNr-NH$_2$ |
| CM1-92 FITC-Onc112-P7 | FITC-K-VDKPPYLPRPRPPRrlYNrG PRQChaDLF-OH |
| CM1-94 FITC-Onc112-P14 | FITC-K-VDKPPYLPRPRPPRrlYNrG PRQChaDLdiCIF-OH |

The aim of this approach is to block the interaction of the bifunctional peptide with the ribosome (through the bulky FITC moiety addition) in order to measure the antimicrobial potential linked directly to the SC binding activity of the peptide.

The lack of interaction with the ribosome of E. coli has been measured by ITC at 30° C.:

| 30° C. | P$_{28}$ Onc112 | CA3 124 FITC-Onc112 | CM1 92 FITC-Onc112-P7 | CM1 94 FITC-Onc112-P14 |
| --- | --- | --- | --- | --- |
| Kd (nM) | 241 (±48) | 7700 | >50,000 | >10,000 |
| ΔH (kcal/mol) | −16.2 (±0.3) | −22.6 | nd | nd |
| ΔG (kcal/mol) | −9.2 (±0.1) | −7.1 (±0.4) | nd | nd | nd: not determined, non-specific interaction.

These experiments show that the presence of an FITC moiety strongly impedes the interaction between the Onc112 peptide and is bacterial ribosome target.

The antimicrobial activities of these peptides have been tested against the E. coli ATCC 25922 (DSM 1103) strain in 1× Mueller-Hinton broth as mentioned above. Minimal Inhibitory Concentrations (MIC) range obtained are listed in the following table:

| | CA3-124 FITC-K-Onc112 | CM1-92 FITC-K-Onc112-P7 | CM1-94 FITC-K-Onc112-P14 |
| --- | --- | --- | --- |
| MIC (μM) | 32-64 | 16 | 4-8 |

These data show that:
1. As compared to the activity of a monofunctional peptide such as a FITC modified PrAMP (CA3-124), the antimicrobial activities of the FITC-PrAMPs-SC fusion peptides are clearly increased. This highlights the antimicrobial activity of SC binding peptides.
2. An increase in SC binding peptides affinity for the SC target (as measured in vitro; cf. Wolff et al. 2011: IC50 for P7=0.17 μM; IC50 for P14=0.077 μM) correlates with an augmented activity in cellulo (MIC values).

Preparation and Activity of Fusion Peptides P2-L-P1

Two fusion peptides in the P2-L-P1 configuration were synthesized: CM1-76 (P7-Onc112) and CM1-122 (P7Scr-Onc112). The aim of this approach is, again, to block the interaction of the Onc112 moiety with the ribosome by hiding its N-terminal extremity thanks to the SC-binding P7 peptide.

| Name | | Sequence |
| --- | --- | --- |
| CM 1-76 | P7-Onc112 | AcQChaDLF-GPR-VDKPPYLPRPR PPRrlYNr-NH2 |
| CM 1-122 | P7Scr-Onc112 | AcChaFQLD-GPR-VDKPPYLPRPR PPRrlYNr-NH2 |

The interactions of these peptides with the E. coli SC (beta ring) and the ribosome were measured by ITC at 25° C.:

Interaction of Fusion Peptides P2-L-P1 with the E. coli SC (Beta Ring)

| 25° C. | Kd (nM) | ΔH (kcal/mol) | ΔG (kcal/mol) | n |
| --- | --- | --- | --- | --- |
| P7 (CA2 68) | 170 (±7) | −15.4 (±0.9) | −9.2 (±0.02) | 0.9 |
| Onc112 (CA3 28) | | no interaction | | |

-continued

| 25° C. | Kd (nM) | ΔH (kcal/mol) | ΔG (kcal/mol) | n |
|---|---|---|---|---|
| Onc112-P7 (CA3-30) | 180 (±50) | −14.6 (±0.8) | −9.2 (±0.1) | 0.9 |
| P7-Onc112 (CM1-76) | 258 (±70) | −10.7 (±0.6) | −9.0 (±0.1) | 1 |
| P7Scr-Onc112 (CM1 122) | — | no interaction | — | — |

The bifunctional peptide CM1-76 (P2-L-P1) interacts as efficiently with the SC as the P7 control peptide or its inverted counterpart CA3-30 (P1-L-P2). As expected, neither the Onc112 nor the scrambled version of P7 interacts with the SC target.

Interaction of Fusion Peptides P2-L-P1 with the *E. coli* Ribosome (70S).

| 25° C. | Kd (nM) | ΔH (kcal/mol) | ΔG(kcal/mol) | n |
|---|---|---|---|---|
| Onc112 (CA3 28) | 241 (±48) | −16.2 (±0.3) | −9.2 (±0.1) | 1 |
| P7-Onc112 (CM1 76) | | no interaction | | — |

These data show that the addition of the SC binding peptide at the N-terminal part of the Onc112 peptide fully prevents its interaction with the ribosome. Thus, the P2-L-P1 configuration allows the binding of the fusion peptide to the SC target but not to the ribosomal target.

The antimicrobial activities of these peptides and controls have been tested against the *E. coli* ATCC 25922 (DSM 1103) strain in 1× Mueller-Hinton broth. Minimal Inhibitory Concentrations (MIC) ranges obtained are listed in the following table:

| | CA3-28 Onc 112 | CA3-30 Onc-P7 | CM1-76 P7-Onc | CM1-122 P7Scr-Onc |
|---|---|---|---|---|
| MIC (μM) | 2-8 | 16-32 | 8-16 | 8->64 |

Given the affinities measured in vitro, these data suggest that the fusion of the P7 peptide to Onc112 (either in the P1-L-P2 or P2-L-P1 orientation) diminish the cell penetration capacity of the fusion peptide (as observed for the FITC-K-Py-P7 fusion peptide as compared to the FITC-K-Py peptide) by at least a factor 2). The P2-L-P1 configuration (CM1-76) improves the antimicrobial activity of the fusion peptide by a factor 2 (CM1-76 versus CA3-30). The data obtained with the CM1-122 (scrambled P7) peptide highlights the contribution of the P7 peptide to the toxicity.

These data illustrate the possibility to exploit the cell penetration capacities of the PrAMPs peptides and the SC-binding capacities of the SC binding peptides by using the P2-L-P1 configuration.

Ability of the Fusion Peptides to Penetrate the Bacterial Cell

The inventors have demonstrated and quantified the cytoplasmic localization of the PrAMPs-SC fusion peptides by using the FITC-K-Py (CA3-122 or $P_{122}$); FITC-K-Py-P7 (CA2-150 or $P_{150}$) and FITC-K-Py-P7Scr (CA4-72 or $P_{72}$) and Confocal Laser Scanning Microscopy (CLSM).

The results are shown in FIG. 3.

In Cellulo Identification of the SC-Binding (P2) Target and their Bacterial Specificity The inventors show by co-immunoprecipitation assays that only the SC-binding FITC-K-Py-P7 fusion peptide but not the FITC-K-Py or the FITC-K-Py-P7Scr can efficiently bind SC within the bacterial cytoplasm (see FIG. 4).

Specificity of the SC-Binding Peptides Toward the Bacterial Sliding Clamp (SC).

The inventors have compared the affinities of the prototypical P7 SC-binding peptide for the bacterial SC and for the eukaryotic functional homolog "Proliferating Cell Nuclear Antigen" PCNA. The same analysis was performed with the DPD1 peptide that contains a well-described specific PCNA Interacting Peptide (PIP) sequence (QK-KITDYF). Results obtained are listed in the following table:

| | *E.coli* SC | | Human PCNA | |
|---|---|---|---|---|
| ITC 30° C. | P7 | DPD1 | P7 | DPD1 |
| Kd (nM) | 408 | — | — | 158 |
| ΔH (kcal/mol) | −12.05 | no interaction | no interaction | −9.94 |
| n | 1 | — | — | 1 |

As no interaction could be detected between PCNA and P7, these results demonstrate the high specificity of the SC binding peptides that we have developed toward their bacterial target. This strongly suggests the safety of these peptides for the eukaryotic replication machinery.

The invention claimed is:
1. A fusion peptide having one of the following formulae:

P1-L-P2 (I) or

P2-L-P1 (II)

wherein:
P1 is a proline-rich antimicrobial peptide;
L is a peptide linker comprising from 1 to 10 amino acids; and
P2 has the following formula (III):

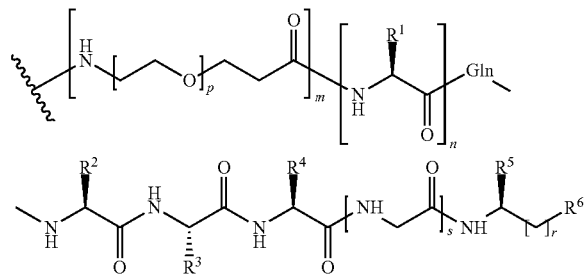

wherein:
m is 0 or 1;
n is an integer comprised between 0 and 9;
p is an integer comprised between 0 and 10;
r is 0, 1 or 2;
s is 0 or 1;
Gln is glutamine;
$R^1$ is the side chain of arginine or lysine;
$R^2$ is a —(CH$_2$)—C$_{3-6}$-cycloalkyl group optionally substituted by a halogen and/or a moiety selected from the group consisting of —NH$_2$, —NH—CO—R$^a$, —CO$_2$H, —NHR$^a$ and —NR$^a$R$^b$, wherein R$^a$ and R$^b$ are independently a C$_{1-4}$-alkyl group;
$R^3$ is selected from the group consisting of a C$_{1-8}$-alkyl group, the side chain of arginine or lysine, —(CH$_2$)$_q$—CO$_2$R$^{7a}$, —(CH$_2$)$_q$—CO—NHR$^{7b}$, —CH$_2$OR$^8$ and —(CH$_2$)$_q$NHR$^9$, wherein
q is 1, 2, 3 or 4,
$R^{7a}$ is a hydrogen atom, a C$_{1-8}$-alkyl group, a C$_{4-12}$-alkylene group forming together with R$^6$ a lactone or a polyether ring, or a C$_{4-12}$-alkenylene, forming together with R$^6$ a lactone or a polyether ring,
$R^{7b}$ is a hydrogen atom, a C$_{1-8}$-alkyl group, or —(CH$_2$)$_{q'}$-NH— with q' being an integer between 2 and 8 inclusive and forming together with R$^6$ a lactam,
$R^8$ is a hydrogen atom, a C$_{1-8}$-alkyl group, a C$_{4-12}$-alkylene group forming together with R$^6$ a lactone or a polyether ring, or a C$_{4-12}$-alkenylene, forming together with R$^6$ a lactone or a polyether ring,
$R^9$ is a hydrogen atom, or R$^9$ together with R$^6$ form a lactam;
$R^4$ is a C$_{1-8}$-alkyl group optionally substituted by a C$_{3-6}$-cycloalkyl group, or a halogen-C$_{1-4}$-alkyl group;
$R^5$ is selected from the group consisting of a —(CH$_2$)—C$_{3-6}$-cycloalkyl group; (CH$_2$—CH$_2$)—C$_{3-6}$-cycloalkyl group; a —(CH$_2$)—C$_{6-10}$-aryl group optionally substituted by a halogen, a C$_{1-12}$ alkyl group and/or a C$_{1-12}$ alkoxy group; a —(CH$_2$—CH$_2$)—C$_{6-10}$-aryl group optionally substituted by a halogen, a C$_{1-2}$ alkyl group and/or a C$_{1-2}$ alkoxy group; a —(CH$_2$)—C$_{5-10}$-heteroaryl group optionally substituted by a halogen and/or a C$_{1-2}$ alkyl group;
$R^6$ is —COOH, —COOR$^{10}$, —CO—NH$_2$, —CO—NHR$^{10}$, —OR$^{10}$ when r is 1 or 2, —NH—CO—NHR$^{10}$ when r is 1 or 2, or R$^6$ is —CO—, —CO—O— or —O— and forms a lactam, a lactone, or a polyether ring with R$^{7a}$, R$^{7b}$, R$^8$ or R$^9$; wherein
$R^{10}$ is a C$_{1-8}$-alkyl group optionally substituted by a C$_{6-10}$-aryl group; a C$_{3-6}$-cycloalkyl group; a C$_{6-10}$-aryl group optionally substituted by a halogen, a C$_{1-2}$-alkyl group and/or a C$_{1-2}$-alkoxy group,
wherein, when the fusion peptide has the formula (II), its C-terminus contains a —CO— group engaged in a peptide bond with said linker L; and
wherein P1 comprises from 13 to 40 amino acid residues and contains at least one peptide consisting of the sequence SEQ ID NO:1:

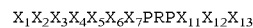

wherein: X$_1$ is V, R or P; X$_2$ is D, R, P or F; X$_3$ is K, P, V or R; X$_4$ is P, G, R, Y, Q or A; X$_5$ is S, G, D, P, I, O or Q; X$_6$ is Y, P, V, I or R; X$_7$ is L, P, Q or R;
X$_{11}$ is P, R, T or G: X$_{12}$ is P, W, H or R; and X$_{13}$ is P, Hyp or R, O being ornithine and Hyp being hydroxyl-proline, and wherein X$_1$-X$_7$ and X$_{11}$-X$_{13}$ can also be D-Arg,
P1 containing optionally at its N-terminus from 0 to 10 amino acid residues and at its C-terminus from 0 to 18 amino acid residues, said amino acid residues being selected from the group consisting of natural L-amino acids, D-amino acids, modified amino acids, non-natural amino acids, and mixtures thereof.

2. The fusion peptide of claim 1, wherein P1 is selected from the group consisting of the following peptides: VDKP-PYLPRPRPPRrIYNr-NH$_2$ (SEQ ID NO: 2), and VDKG-SYLPRPTPPRPIYNRN (SEQ ID NO: 3), r representing D-arginine.

3. The fusion peptide according to claim 1, wherein L is selected from the group consisting of the following amino acids or peptides: Gly-Pro,Gly-Gly, Pro-Gly, β-Ala-ρ-Ala, Sar-Sar, Gly-Glycolic acid, γ-Abu, 6-aminohexanoic acid, aminovaleric acid, and Gly-Gly-Gly.

4. The fusion peptide according to claim 1, wherein P2 has the following formula (IV):

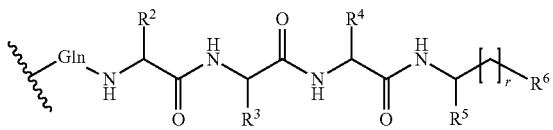

wherein R$^2$, R$^3$, R$^4$, R$^5$, R$^6$, and r are as defined in claim 1.

5. The fusion peptide according to claim 4, wherein, in formula (IV), r=0.

6. The fusion peptide according to claim 4, wherein, in formula (III), R$^2$ is a —(CH$_2$)—C$_{3-6}$-cycloalkyl group or a methylcyclohexane —(CH$_2$)—C$_6$H$_{11}$ group.

7. The fusion peptide according to claim 4, wherein, in formula (III):
R$^3$ is selected from the group consisting of a C$_{1-8}$-alkyl group, the side chain of arginine or lysine, —(CH$_2$)$_q$—CO$_2$R$^{7a}$, —(CH$_2$)$_q$—CO—NHR$^{7b}$, —CH$_2$OR$^8$ and —(CH$_2$)$_q$NHR$^9$, wherein q is 1, 2, 3 or 4,
$R^{7a}$ is a hydrogen atom or a $C_{1-8}$-alkyl group,
$R^{7b}$ is a hydrogen atom or a $C_{1-8}$-alkyl group,
$R^8$ is a hydrogen atom or a $C_{1-8}$-alkyl group,
$R^9$ is a hydrogen atom; and
$R^6$ is —COOH, —COOR$^{10}$, —CO—NH$_2$, —CO—NHR$^{10}$, —OR$^{10}$ when r is 1 or 2, —NH—CO—NHR$^{10}$ when r is 1 or 2, wherein
$R^{10}$ is a $C_{1-8}$-alkyl group optionally substituted by a $C_{6-10}$-aryl group; a $C_{3-6}$-cycloalkyl group; a $C_{6-10}$-aryl group optionally substituted by a halogen, a $C_{1-2}$-alkyl group and/or a $C_{1-2}$-alkoxy group.

8. The fusion peptide according to claim 4, wherein, in formula (III):
$R^3$ is selected from the group consisting of the side chain of arginine, the side chain of lysine, —(CH$_2$)$_q$—CO$_2$R$^{7a}$, and —(CH$_2$)$_q$—CO—NHR$^{7b}$, wherein
q is 1, 2, 3 or 4,
$R^{7a}$ is a hydrogen atom or a $C_{1-8}$-alkyl group, and
$R^{7b}$ is a hydrogen atom or a $C_{1-8}$-alkyl group.

9. The fusion peptide according to claim 4, wherein, in formula (III), $R^4$ is a $C_{1-5}$-alkyl group or a $C_{1-2}$-alkyl group optionally substituted by a $C_{3-6}$-cycloalkyl group.

10. The fusion peptide according to claim 4, wherein, in formula (III), $R^5$ is a —(CH$_2$)—C$_{6-10}$-aryl group optionally substituted by a halogen, a $C_{1-2}$ alkyl group and/or a $C_{1-2}$ alkoxy group.

11. The fusion peptide according to claim 4, wherein, in formula (III), $R^6$ is —COOH or —CO—NH$_2$.

12. The fusion peptide according to claim 1, wherein P2 is selected from the group consisting of following peptides: (Arg)$_n$-Gln-Cha-Asp-Leu-Phe-OH (SEQ ID NO: 28), Cha representing cyclohexylalanine, (Arg)$_n$-Gln-Cha-Asp-Leu-pMePhe-OH (SEQ ID NO: 29), Gln-Cha-Asp-Leu-pClPhe-OH (SEQ ID NO: 30), (Arg)$_n$-Gln-Cha-Asp-Leu-3,4-Cl$_2$Phe-OH (SEQ ID NO: 31), (Arg)$_n$-Gln-Cha-Asp-Leu-pBrPhe-OH (SEQ ID NO: 32), (D-Arg)$_n$-Gln-Cha-Asp-Leu-Phe-OH, Cha representing cyclohexylalanine, (D-Arg)$^n$-Gln-Cha-Asp-Leu-pMePhe-OH, (D-Arg)$_n$-Gln-Cha-Asp-Leu-3,4-Cl$_2$Phe-OH, and (D-Arg)$_n$-Gln-Cha-Asp-Leu-pBrPhe-OH),n being 0 or 1.

13. A medicament comprising a fusion peptide according to claim 1.

14. The fusion peptide according to claim 1 for use for the treatment of bacterial infections.

15. The fusion peptide of claim 1, wherein L comprises from 2 to 3 amino acids.

16. The fusion peptide of claim 1, wherein L contains any natural amino acid.

17. The fusion peptide of claim 1, wherein L comprises an amino acid selected from the group consisting of A, G, P, S, D, E, V and leucine.

18. The fusion peptide of claim 1, wherein L has the sequence GPR.

* * * * *

SEQUENCE LISTING

```
<160> NUMBER OF SEQ ID NOS: 27

<210> SEQ ID NO 1
<211> LENGTH: 13
<212> TYPE: PRT
<213> ORGANISM: Artificial Sequence
<220> FEATURE:
<223> OTHER INFORMATION: central segment
<220> FEATURE:
<221> NAME/KEY: MISC_FEATURE
<222> LOCATION: (1)..(1)
<223> OTHER INFORMATION: V, R or P
<220> FEATURE:
<221> NAME/KEY: MISC_FEATURE
<222> LOCATION: (2)..(2)
<223> OTHER INFORMATION: D, R, P or F
<220> FEATURE:
<221> NAME/KEY: MISC_FEATURE
<222> LOCATION: (3)..(3)
<223> OTHER INFORMATION: K, P, V or R
```

```
-continued

<220> FEATURE:
<221> NAME/KEY: MISC_FEATURE
<222> LOCATION: (4)..(4)
<223> OTHER INFORMATION: P, G, R, Y, Q or A
<220> FEATURE:
<221> NAME/KEY: MISC_FEATURE
<222> LOCATION: (5)..(5)
<223> OTHER INFORMATION: S, G, D, P, I, Orn or Q
<220> FEATURE:
<221> NAME/KEY: MISC_FEATURE
<222> LOCATION: (6)..(6)
<223> OTHER INFORMATION: Y, P, V, I or R
<220> FEATURE:
<221> NAME/KEY: MISC_FEATURE
<222> LOCATION: (7)..(7)
<223> OTHER INFORMATION: L, P, Q or R
<220> FEATURE:
<221> NAME/KEY: MISC_FEATURE
<222> LOCATION: (11)..(11)
<223> OTHER INFORMATION: P, R, T or G
<220> FEATURE:
<221> NAME/KEY: MISC_FEATURE
<222> LOCATION: (12)..(12)
<223> OTHER INFORMATION: P, W, H or R
<220> FEATURE:
<221> NAME/KEY: MISC_FEATURE
<222> LOCATION: (13)..(13)
<223> OTHER INFORMATION: P, Hyp or R
<220> FEATURE:
<221> NAME/KEY: MISC_FEATURE
<222> LOCATION: (13)..(13)
<223> OTHER INFORMATION: P, hydroxyproline or R

<400> SEQUENCE: 1

Xaa Xaa Xaa Xaa Xaa Xaa Xaa Pro Arg Pro Xaa Xaa Xaa
1               5                   10

<210> SEQ ID NO 2
<211> LENGTH: 19
<212> TYPE: PRT
<213> ORGANISM: Artificial Sequence
<220> FEATURE:
<223> OTHER INFORMATION: Onc112
<220> FEATURE:
<221> NAME/KEY: MISC_FEATURE
<222> LOCATION: (15)..(15)
<223> OTHER INFORMATION: D-arginine
<220> FEATURE:
<221> NAME/KEY: MOD_RES
<222> LOCATION: (19)..(19)
<223> OTHER INFORMATION: AMIDATION
<220> FEATURE:
<221> NAME/KEY: MISC_FEATURE
<222> LOCATION: (19)..(19)
<223> OTHER INFORMATION: D-arginine

<400> SEQUENCE: 2

Val Asp Lys Pro Pro Tyr Leu Pro Arg Pro Arg Pro Pro Arg Xaa Ile
1               5                   10                  15

Tyr Asn Xaa

<210> SEQ ID NO 3
<211> LENGTH: 20
<212> TYPE: PRT
<213> ORGANISM: Artificial Sequence
<220> FEATURE:
<223> OTHER INFORMATION: Pyrrhocoricin

<400> SEQUENCE: 3

Val Asp Lys Gly Ser Tyr Leu Pro Arg Pro Thr Pro Pro Arg Pro Ile
1               5                   10                  15

Tyr Asn Arg Asn
```

```
<210> SEQ ID NO 4
<211> LENGTH: 18
<212> TYPE: PRT
<213> ORGANISM: Artificial Sequence
<220> FEATURE:
<223> OTHER INFORMATION: Apidaecin-1b

<400> SEQUENCE: 4

Gly Asn Asn Arg Pro Val Tyr Ile Pro Gln Pro Arg Pro Pro His Pro
1               5                   10                  15

Arg Leu

<210> SEQ ID NO 5
<211> LENGTH: 18
<212> TYPE: PRT
<213> ORGANISM: Artificial Sequence
<220> FEATURE:
<223> OTHER INFORMATION: Api137
<220> FEATURE:
<221> NAME/KEY: MISC_FEATURE
<222> LOCATION: (1)..(1)
<223> OTHER INFORMATION: Orn modified by a N,N,N',N'-
      tetramethylguanidino group (gu)

<400> SEQUENCE: 5

Xaa Asn Asn Arg Pro Val Tyr Ile Pro Gln Pro Arg Pro Pro His Pro
1               5                   10                  15

Arg Leu

<210> SEQ ID NO 6
<211> LENGTH: 18
<212> TYPE: PRT
<213> ORGANISM: Artificial Sequence
<220> FEATURE:
<223> OTHER INFORMATION: Api88
<220> FEATURE:
<221> NAME/KEY: MISC_FEATURE
<222> LOCATION: (1)..(1)
<223> OTHER INFORMATION: Orn modified by a N,N,N',N'-
      tetramethylguanidino group (gu)
<220> FEATURE:
<221> NAME/KEY: MOD_RES
<222> LOCATION: (18)..(18)
<223> OTHER INFORMATION: AMIDATION

<400> SEQUENCE: 6

Xaa Asn Asn Arg Pro Val Tyr Ile Pro Gln Pro Arg Pro Pro His Pro
1               5                   10                  15

Arg Leu

<210> SEQ ID NO 7
<211> LENGTH: 24
<212> TYPE: PRT
<213> ORGANISM: Artificial Sequence
<220> FEATURE:
<223> OTHER INFORMATION: Api794
<220> FEATURE:
<221> NAME/KEY: MISC_FEATURE
<222> LOCATION: (1)..(1)
<223> OTHER INFORMATION: Orn modified by a N,N,N',N'-
      tetramethylguanidino group (gu)
<220> FEATURE:
<221> NAME/KEY: MISC_FEATURE
<222> LOCATION: (3)..(3)
<223> OTHER INFORMATION: Orn
<220> FEATURE:
<221> NAME/KEY: MISC_FEATURE
```

```
<222> LOCATION: (5)..(5)
<223> OTHER INFORMATION: Orn
<220> FEATURE:
<221> NAME/KEY: MISC_FEATURE
<222> LOCATION: (7)..(7)
<223> OTHER INFORMATION: Orn
<220> FEATURE:
<221> NAME/KEY: MISC_FEATURE
<222> LOCATION: (9)..(9)
<223> OTHER INFORMATION: Orn

<400> SEQUENCE: 7

Xaa Trp Xaa Trp Xaa Trp Xaa Trp Xaa Arg Pro Val Tyr Ile Pro Gln
1               5                   10                  15

Pro Arg Pro Pro His Pro Arg Leu
            20

<210> SEQ ID NO 8
<211> LENGTH: 32
<212> TYPE: PRT
<213> ORGANISM: Artificial Sequence
<220> FEATURE:
<223> OTHER INFORMATION: Abaecin

<400> SEQUENCE: 8

Tyr Val Pro Leu Pro Asn Val Pro Gln Pro Gly Arg Arg Pro Phe Pro
1               5                   10                  15

Thr Phe Pro Gly Gln Gly Pro Phe Asn Pro Lys Ile Lys Trp Pro Gln
            20                  25                  30

<210> SEQ ID NO 9
<211> LENGTH: 19
<212> TYPE: PRT
<213> ORGANISM: Artificial Sequence
<220> FEATURE:
<223> OTHER INFORMATION: Drosocin

<400> SEQUENCE: 9

Gly Lys Pro Arg Pro Tyr Ser Pro Arg Pro Thr Ser His Pro Arg Pro
1               5                   10                  15

Ile Arg Val

<210> SEQ ID NO 10
<211> LENGTH: 17
<212> TYPE: PRT
<213> ORGANISM: Artificial Sequence
<220> FEATURE:
<223> OTHER INFORMATION: Ho+

<400> SEQUENCE: 10

Gly Lys Pro Arg Pro Gln Gln Val Pro Pro Arg Pro Pro His Pro Arg
1               5                   10                  15

Leu

<210> SEQ ID NO 11
<211> LENGTH: 20
<212> TYPE: PRT
<213> ORGANISM: Artificial Sequence
<220> FEATURE:
<223> OTHER INFORMATION: Cd1+

<400> SEQUENCE: 11

Gly Lys Pro Asn Arg Pro Arg Pro Ala Pro Ile Gln Pro Arg Pro Pro
1               5                   10                  15

His Pro Arg Leu
```

<210> SEQ ID NO 12
<211> LENGTH: 25
<212> TYPE: PRT
<213> ORGANISM: Artificial Sequence
<220> FEATURE:
<223> OTHER INFORMATION: Arasin 1

<400> SEQUENCE: 12

Ser Arg Trp Pro Ser Pro Gly Arg Pro Arg Pro Phe Pro Gly Arg Pro
1               5                   10                  15

Lys Pro Ile Phe Arg Pro Arg Pro Cys
            20                  25

<210> SEQ ID NO 13
<211> LENGTH: 20
<212> TYPE: PRT
<213> ORGANISM: Artificial Sequence
<220> FEATURE:
<223> OTHER INFORMATION: Oncocin
<220> FEATURE:
<221> NAME/KEY: misc_feature
<222> LOCATION: (11)..(11)
<223> OTHER INFORMATION: Xaa can be any naturally occurring amino acid

<400> SEQUENCE: 13

Val Asp Lys Pro Pro Tyr Leu Pro Arg Pro Xaa Pro Pro Arg Arg Ile
1               5                   10                  15

Tyr Asn Asn Arg
            20

<210> SEQ ID NO 14
<211> LENGTH: 19
<212> TYPE: PRT
<213> ORGANISM: Artificial Sequence
<220> FEATURE:
<223> OTHER INFORMATION: Onc72
<220> FEATURE:
<221> NAME/KEY: MISC_FEATURE
<222> LOCATION: (15)..(15)
<223> OTHER INFORMATION: D-arginine
<220> FEATURE:
<221> NAME/KEY: MISC_FEATURE
<222> LOCATION: (16)..(16)
<223> OTHER INFORMATION: Orn
<220> FEATURE:
<221> NAME/KEY: MISC_FEATURE
<222> LOCATION: (19)..(19)
<223> OTHER INFORMATION: Orn
<220> FEATURE:
<221> NAME/KEY: MOD_RES
<222> LOCATION: (19)..(19)
<223> OTHER INFORMATION: AMIDATION

<400> SEQUENCE: 14

Val Asp Lys Pro Pro Tyr Leu Pro Arg Pro Arg Pro Pro Arg Xaa Xaa
1               5                   10                  15

Tyr Asn Xaa

<210> SEQ ID NO 15
<211> LENGTH: 19
<212> TYPE: PRT
<213> ORGANISM: Artificial Sequence
<220> FEATURE:
<223> OTHER INFORMATION: Onc06
<220> FEATURE:
<221> NAME/KEY: MISC_FEATURE
<222> LOCATION: (13)..(13)

```
<223> OTHER INFORMATION: Hydroxyproline
<220> FEATURE:
<221> NAME/KEY: MISC_FEATURE
<222> LOCATION: (15)..(15)
<223> OTHER INFORMATION: Hydroxyproline
<220> FEATURE:
<221> NAME/KEY: MISC_FEATURE
<222> LOCATION: (16)..(16)
<223> OTHER INFORMATION: L-tert-Leucine
<220> FEATURE:
<221> NAME/KEY: MOD_RES
<222> LOCATION: (19)..(19)
<223> OTHER INFORMATION: AMIDATION
<220> FEATURE:
<221> NAME/KEY: MISC_FEATURE
<222> LOCATION: (19)..(19)
<223> OTHER INFORMATION: Orn

<400> SEQUENCE: 15

Val Asp Lys Pro Pro Tyr Leu Pro Arg Pro Arg Pro Xaa Arg Xaa Xaa
1               5                   10                  15

Tyr Asn Xaa

<210> SEQ ID NO 16
<211> LENGTH: 19
<212> TYPE: PRT
<213> ORGANISM: Artificial Sequence
<220> FEATURE:
<223> OTHER INFORMATION: Onc15
<220> FEATURE:
<221> NAME/KEY: MOD_RES
<222> LOCATION: (19)..(19)
<223> OTHER INFORMATION: AMIDATION

<400> SEQUENCE: 16

Val Asp Lys Pro Pro Tyr Leu Pro Arg Pro Arg Trp Pro Arg Arg Ile
1               5                   10                  15

Tyr Asn Arg

<210> SEQ ID NO 17
<211> LENGTH: 15
<212> TYPE: PRT
<213> ORGANISM: Artificial Sequence
<220> FEATURE:
<223> OTHER INFORMATION: Metalnikowin-1

<400> SEQUENCE: 17

Val Asp Lys Pro Asp Tyr Arg Pro Arg Pro Arg Pro Pro Asn Met
1               5                   10                  15

<210> SEQ ID NO 18
<211> LENGTH: 19
<212> TYPE: PRT
<213> ORGANISM: Artificial Sequence
<220> FEATURE:
<223> OTHER INFORMATION: Riptocin

<400> SEQUENCE: 18

Val Asp Lys Gly Gly Tyr Leu Pro Arg Pro Thr Pro Pro Arg Pro Val
1               5                   10                  15

Tyr Arg Ser

<210> SEQ ID NO 19
<211> LENGTH: 25
<212> TYPE: PRT
<213> ORGANISM: Artificial Sequence
<220> FEATURE:
<223> OTHER INFORMATION: bt-bactenecin-7
```

```
<400> SEQUENCE: 19

Arg Arg Ile Arg Pro Arg Pro Pro Arg Leu Pro Arg Pro Arg Pro Arg
1               5                   10                  15

Pro Leu Pro Phe Pro Arg Pro Gly Pro
            20                  25

<210> SEQ ID NO 20
<211> LENGTH: 25
<212> TYPE: PRT
<213> ORGANISM: Artificial Sequence
<220> FEATURE:
<223> OTHER INFORMATION: ch-bactenecin-7

<400> SEQUENCE: 20

Arg Arg Leu Arg Pro Arg Arg Pro Arg Leu Pro Arg Pro Arg Pro Arg
1               5                   10                  15

Pro Arg Pro Arg Pro Arg Ser Leu Pro
            20                  25

<210> SEQ ID NO 21
<211> LENGTH: 25
<212> TYPE: PRT
<213> ORGANISM: Artificial Sequence
<220> FEATURE:
<223> OTHER INFORMATION: oa-bactenecin-7

<400> SEQUENCE: 21

Arg Arg Leu Arg Pro Arg Arg Pro Arg Leu Pro Arg Pro Arg Pro Arg
1               5                   10                  15

Pro Arg Pro Arg Pro Arg Ser Leu Pro
            20                  25

<210> SEQ ID NO 22
<211> LENGTH: 25
<212> TYPE: PRT
<213> ORGANISM: Artificial Sequence
<220> FEATURE:
<223> OTHER INFORMATION: PR-39

<400> SEQUENCE: 22

Arg Arg Arg Pro Arg Pro Pro Tyr Leu Pro Arg Pro Arg Pro Pro Pro
1               5                   10                  15

Phe Phe Pro Pro Arg Leu Pro Pro Arg
            20                  25

<210> SEQ ID NO 23
<211> LENGTH: 25
<212> TYPE: PRT
<213> ORGANISM: Artificial Sequence
<220> FEATURE:
<223> OTHER INFORMATION: bt-bactenecin-5

<400> SEQUENCE: 23

Arg Phe Arg Pro Pro Ile Arg Arg Pro Pro Ile Arg Pro Pro Phe Tyr
1               5                   10                  15

Pro Pro Phe Arg Pro Pro Ile Arg Pro
            20                  25

<210> SEQ ID NO 24
<211> LENGTH: 25
<212> TYPE: PRT
<213> ORGANISM: Artificial Sequence
<220> FEATURE:
```

<223> OTHER INFORMATION: ch-bactenecin-5

<400> SEQUENCE: 24

Arg Phe Arg Pro Pro Ile Arg Arg Pro Pro Ile Arg Pro Pro Phe Asn
1               5                   10                  15

Pro Pro Phe Arg Pro Pro Val Arg Pro
            20                  25

<210> SEQ ID NO 25
<211> LENGTH: 25
<212> TYPE: PRT
<213> ORGANISM: Artificial Sequence
<220> FEATURE:
<223> OTHER INFORMATION: oa-bactenecin-5

<400> SEQUENCE: 25

Arg Phe Arg Pro Pro Ile Arg Arg Pro Pro Ile Arg Pro Pro Phe Arg
1               5                   10                  15

Pro Pro Phe Arg Pro Pro Val Arg Pro
            20                  25

<210> SEQ ID NO 26
<211> LENGTH: 35
<212> TYPE: PRT
<213> ORGANISM: Artificial Sequence
<220> FEATURE:
<223> OTHER INFORMATION: Bac7(1-35)

<400> SEQUENCE: 26

Arg Arg Ile Arg Pro Arg Pro Pro Arg Leu Pro Arg Pro Arg Pro Arg
1               5                   10                  15

Pro Leu Pro Phe Pro Arg Pro Gly Pro Arg Pro Ile Pro Arg Pro Leu
            20                  25                  30

Pro Phe Pro
        35

<210> SEQ ID NO 27
<211> LENGTH: 32
<212> TYPE: PRT
<213> ORGANISM: Artificial Sequence
<220> FEATURE:
<223> OTHER INFORMATION: Tur1A

<400> SEQUENCE: 27

Arg Arg Ile Arg Phe Arg Pro Pro Tyr Leu Pro Arg Pro Gly Arg Arg
1               5                   10                  15

Pro Arg Phe Pro Pro Pro Phe Pro Ile Pro Arg Ile Pro Arg Ile Pro
            20                  25                  30